United States Patent
Sasaki et al.

(10) Patent No.: US 6,664,361 B2
(45) Date of Patent: Dec. 16, 2003

(54) DIPHENOL COMPOUND, AROMATIC POLYCARBONATE AND ELECTROPHOTOCONDUCTIVE PHOTOCONDUCTOR

(75) Inventors: Masaomi Sasaki, Susono (JP); Shinichi Kawamura, Yokohama (JP); Kazukiyo Nagai, Numazu (JP); Kohkoku Ri, Numazu (JP); Katsuhiro Morooka, Kawasaki (JP); Susumu Suzuka, Kawasaki (JP)

(73) Assignee: Ricoh Company, Ltd., Tokyo (JP)

( * ) Notice: Subject to any disclaimer, the term of this patent is extended or adjusted under 35 U.S.C. 154(b) by 41 days.

(21) Appl. No.: 10/000,082

(22) Filed: Dec. 4, 2001

(65) Prior Publication Data

US 2002/0147278 A1 Oct. 10, 2002

(30) Foreign Application Priority Data

Dec. 4, 2000 (JP) ........................ 2000-368297

(51) Int. Cl.$^7$ .............................. C08G 64/00

(52) U.S. Cl. .................. 528/196; 430/58.7; 430/56.1; 430/66; 430/96; 528/198

(58) Field of Search ................. 528/196, 198; 430/58.7, 561, 66, 96

(56) References Cited

U.S. PATENT DOCUMENTS

| | | | |
|---|---|---|---|
| 5,723,243 A | 3/1998 | Sasaki et al. | |
| 5,747,204 A | 5/1998 | Anzai et al. | |
| 5,789,128 A | 8/1998 | Adachi et al. | |
| 5,840,454 A | 11/1998 | Nagai et al. | |
| 5,846,680 A | 12/1998 | Adachi et al. | |
| 5,942,363 A | 8/1999 | Tanaka et al. | |
| 5,976,746 A | 11/1999 | Tamaka et al. | |
| 6,026,262 A | 2/2000 | Kinoshita et al. | |
| 6,027,846 A * | 2/2000 | Shimada et al. | 430/58.7 |
| 6,030,736 A | 2/2000 | Ikegami et al. | |
| 6,045,959 A | 4/2000 | Katayama et al. | |
| 6,066,428 A | 5/2000 | Katayama et al. | |
| 6,093,784 A | 7/2000 | Tamura et al. | |
| 6,136,483 A | 10/2000 | Suzuki et al. | |
| 6,187,492 B1 | 2/2001 | Ri et al. | |
| 6,187,494 B1 | 2/2001 | Kawamura et al. | |
| 6,210,848 B1 | 4/2001 | Nagai et al. | |
| 6,326,112 B1 | 12/2001 | Tamura et al. | |
| 6,444,387 B2 | 9/2002 | Ri et al. | |

* cited by examiner

Primary Examiner—Terressa M. Boykin
(74) Attorney, Agent, or Firm—Oblon, Spivak, McClelland, Maier & Neustadt, P.C.

(57) ABSTRACT

An electrophotographic photoconductor having an electroconductive support, and a photoconductive layer formed thereon and containing an aromatic polycarbonate resin having a structural unit of formula (3) shown in the specification. The polycarbonate resin is produced from a diphenol compound of the formula (1) shown in the specification.

19 Claims, 13 Drawing Sheets

DIPHENOL COMPOUND, AROMATIC POLYCARBONATE AND ELECTROPHOTOCONDUCTIVE PHOTOCONDUCTOR

BACKGROUND OF THE INVENTION

1. Field of the Invention

This invention relates to a novel diphenol compound and to a novel aromatic polycarbonate resin containing diol units from the diphenol compound. The present invention is also directed to an electrophotographic photoconductor having an electroconductive support and a photoconductive layer formed thereon and containing the above aromatic polycarbonate resin which has charge transporting properties.

2. Description of Prior Art

Recently organic photoconductors (OPC) are used in many copying machines and printers. The organic photoconductor has a layered structure comprising a charge generation layer (CGL) and a charge transport layer (CTL) which are successively overlaid on an electroconductive support. The charge transport layer (CTL) is a film-shaped layer comprising a binder resin and a low-molecular-weight charge transport material (CTM) dissolved therein. The addition of such a low-molecular-weight charge transport material (CTM) to the binder resin lowers the intrinsic mechanical strength of the binder resin, so that the CTL film is fragile and has a low tensile strength. Such lowering of the mechanical strength of the CTL causes the wearing of the photoconductor or forms scratches and cracks on the surface of the photoconductor.

Although some vinyl polymers such as polyvinyl anthracene, polyvinyl pyrene and poly-N-vinylcarbazole have been studied as high-molecular-weight photoconductive materials for forming a charge transporting complex for use in the conventional organic photoconductor, such polymers are not satisfactory from the viewpoint of photosensitivity.

In addition, high-molecular-weight materials having charge transporting properties have been also studied to eliminate the shortcomings of the above-mentioned layered photoconductor. For instance, there are proposed an acrylic resin having a triphenylamine structure as reported by M. Stolka et al., in "J. Polym. Sci., vol 21, 969 (1983)"; a vinyl polymer having a hydrazone structure as described in "Japan Hard Copy '89 p. 67"; an aromatic polycarbonate resin having a benzidine structure as disclosed in Japanese Laid-Open Patent Application 64-9964; and polycarbonate resins having a triarylamine structure as disclosed in U.S. Pat. Nos. 4,801,517, 4,806,443, 4,806,444, 4,937,165, 4,959,288, 5,030,532, 5,034,296, and 5,080,989, and Japanese Laid-Open Patent Applications Nos. 64-9964, 3-221522, 2-304456, 4-11627, 4-175337, 4-18371, 4-31404, and 4-133065. However, any materials have not yet been put to practical use.

According to the report of "Physical Review B46 6705 (1992)" by M. A. Abkowitz et al., it is confirmed that the drift mobility of a high-molecular weight charge transport material is lower than that of a low-molecular weight material by one figure. This report is based on the comparison between the photoconductor containing a low-molecular weight tetraarylbenzidine derivative dispersed in the photoconductive layer and the one containing a high-molecular polycarbonate having a tetraarylbenzidine-containing skeleton in its molecule and suggests that the photoconductor employing the high-molecular weight charge transport material produces poor results in terms of the photosensitivity and the residual potential although the mechanical strength of the photoconductor is improved.

SUMMARY OF THE INVENTION

The reason for poor results in the photosensitivity and the residual potential caused by use of the high-molecular weight charge transport material has not yet been clarified. It is, however, inferred that, in a polycarbonate having a tetraarylbenzidine-containing skeleton, the presence of electron-attracting carbonyloxy groups and electron-donating tertiary amino groups on the aryl groups causes localization of electrons, which adversely affects the hole transfer.

In accordance with one aspect of the present invention there is provided a diphenol compound comprising: at least one triarylamine group, two divalent alkane groups each having two, first and second bonds, said first bond of each of said alkane groups being bonded to respective one of the aryl groups of said at least one triarylamine group, an aryl group bonded to the second bond of each of said two alkane groups, and a hydroxyl group bonded to the aryl group linked to each of said two alkane groups.

In another aspect, the present invention provides a diphenol compound represented by the following formula (1):

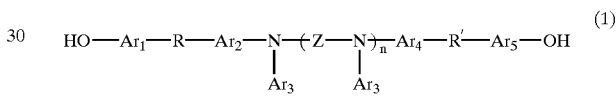
(1)

wherein $Ar_1$, $Ar_2$, $Ar_4$ and $Ar_5$ stand, independently from each other, for an arylene group or a substituted arylene group, $Ar_3$ stands for an aryl group or a substituted aryl group, Z stands for an arylene group or —$Ar_6$—Za—$Ar_6$— where $Ar_6$ represents an arylene group or a substituted arylene group and Za represents —O—, —S— or an alkylene group, R and R' stand, independently from each other, for a straight chain alkylene group or a branched alkylene group and n is an integer of 0 or 1.

The present invention also provides an aromatic polycarbonate resin comprising a main structural unit represented by the following formula (3):

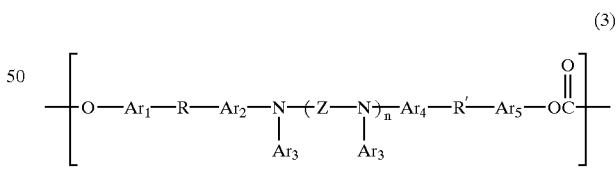
(3)

wherein $Ar_1$, $Ar_2$, $Ar_4$ and $Ar_5$ stand, independently from each other, for an arylene group or a substituted arylene group, $Ar_3$ stands for an aryl group or a substituted aryl group, Z stands for an arylene group or —$Ar_6$—Za—$Ar_6$— where $Ar_6$ represents an arylene group or a substituted arylene group and Za represents —O—, —S— or an alkylene group, R and R' stand, independently from each other, for a straight chain alkylene group or a branched alkylene group and n is an integer of 0 or 1.

The present invention further provides a polycarbonate resin comprising a recurring unit represented by the following formula (6):

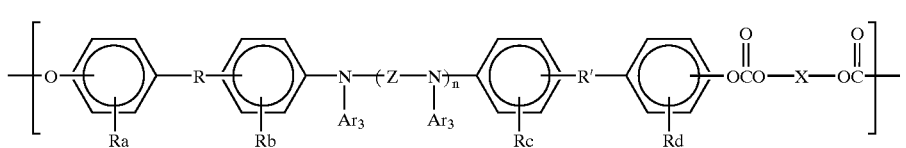

wherein Ra, Rb, Rc and Rd stand for an alkyl group, Ar$_3$ stands for an aryl group or a substituted aryl group, Z stands for an arylene group or —Ar$_6$—Za—Ar$_6$— where Ar$_6$ represents an arylene group or a substituted arylene group and Za represents —O—, —S— or an alkylene group, R and R' stand, independently from each other, for a straight chain alkylene group or a branched alkylene group, n is an integer of 0 or 1 and X stands for a group selected from the group consisting of divalent aliphatic groups, substituted divalent aliphatic groups, divalent alicyclic groups, substituted divalent alicyclic groups, divalent aromatic groups, substituted divalent aromatic groups, divalent groups obtained by linking at least two of the foregoing groups and groups represented by the following formulas:

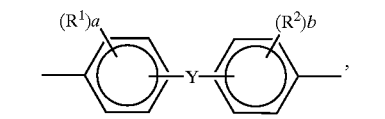

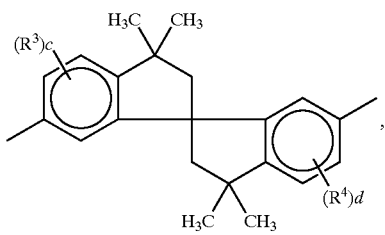

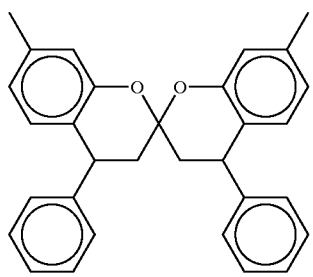

wherein R$^1$, R$^2$, R$^3$ and R$^4$ stand, independently from each other, for an alkyl group, a substituted alkyl group, an aryl group, a substituted aryl group or a halogen atom, a and b are independently an integer of 0–4, c and d are independently an integer of 0–3, Y is selected from the group consisting of a direct bond, straight chain alkylene groups having 2–12 carbon atoms, substituted straight chain alkylene groups having 2–12 carbon atoms, branched A chain alkylene groups having 3–12 carbon atoms, substituted branched chain alkylene groups having 3–12 carbon atoms, divalent groups composed of at least one alkylene group having 1–10 carbon atoms and at least one —O— or at least one —S—, —O—, —S—, —SO—, —SO$_2$—, —CO—, —COO— and groups represented by the following formulas:

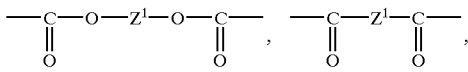

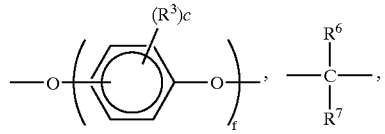

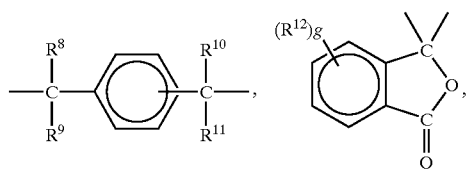

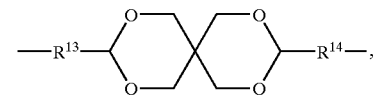

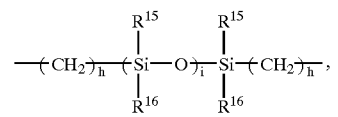

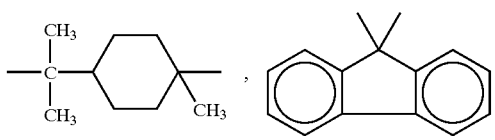

wherein Z$^1$ and Z$^2$ stand independently from each other for a divalent aliphatic group, a substituted divalent aliphatic group, an arylene group or a substituted arylene group; R$^5$$_1$ R$^6$ and R$^{12}$ stand independently from each other for a halogen atom, an alkyl group, a substituted alkyl group, an alkoxyl group, a substituted alkoxyl group, an aryl group or a substituted aryl group, R$^7$, R$^8$, R$^9$, R$^{10}$ and R$^{11}$ stand independently from each other for a hydrogen atom, R$^6$ and R$^7$ may form a carbocyclic ring having 5 to 12 carbon atoms together, R$^{13}$ and R$^{14}$ stand independently from each other for a direct bond or an alkylene group having 1–4 carbon atoms, R$^{15}$ and R$^{16}$ stand independently from each other an alkyl group, a substituted alkyl group, an aryl group or a substituted aryl group, e and g are each an integer of 0–4, f is an integer of 1 or 2, h is an integer of 0–20 and i is an integer of 0–2000.

The present invention further provides an electrographic photoconductor comprising an electroconductive support, and a photoconductive layer provided on said support and containing an aromatic polycarbonate resin including at least one triarylamine group, two divalent alkane groups each having two, first and second bonds, said first bond of each of said alkane groups being bonded to respective one of the aryl groups of said at least one triarylamine group, an aryl group bonded to the second bond of each of said two alkane groups, a —O— group bonded to the aryl group of one of said two alkane groups to form an aryl—O— group, and an oxycarbonyl group —O—CO— bonded to the aryl group of the other one of said two alkane groups to form aryl —O—CO— group.

The present invention further provides an electrographic photoconductor comprising an electroconductive support, and a photoconductive layer provided on said support and containing an aromatic polycarbonate resin comprising a main structural unit represented by the following formula (3):

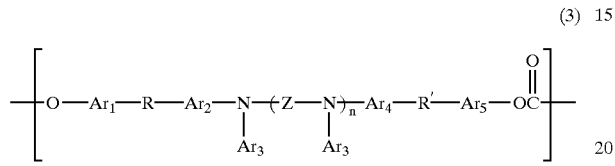

(3)

wherein $Ar_1$, $Ar_2$, $Ar_4$ and $Ar_5$ stand, independently from each other, for an arylene group or a substituted arylene group, $Ar_3$ stands for an aryl group or a substituted aryl group, Z stands for an arylene group or —$Ar_6$—Za—$Ar_6$— where $Ar_6$ represents an arylene group or a substituted arylene group and Za represents —O—, —S— or an alkylene group, R and R' stand, independently from each other, for a straight chain alkylene group or a branched alkylene group and n is an integer of 0 or 1.

The present invention further provides an electrographic photoconductor comprising an electroconductive support, and a photoconductive layer provided on said support and comprising a polycarbonate resin having a recurring unit represented by the following formula (6):

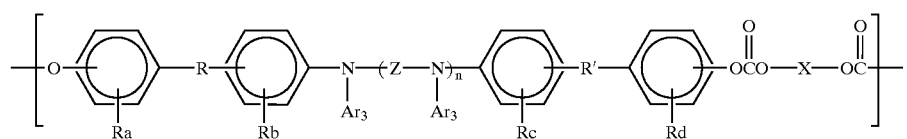

(6)

wherein Ra, Rb, Rc and Rd stand for an alkyl group, $Ar_3$ stands for an aryl group or a substituted aryl group, Z stands for an arylene group or —$Ar_6$—Za—$Ar_6$— where $Ar_6$ represents an arylene group or a substituted arylene group and Za represents —O—, —S— or an alkylene group, R and R' stand, independently from each other, for a straight chain alkylene group or a branched alkylene group, n is an integer of 0 or 1 and X stands for a group selected from the group consisting of divalent aliphatic groups, substituted divalent aliphatic groups, divalent alicyclic groups, substituted divalent alicyclic groups, divalent aromatic groups, substituted divalent aromatic groups, divalent groups obtained by linking at least two of the foregoing groups and groups represented by the following formulas:

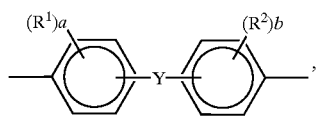

-continued

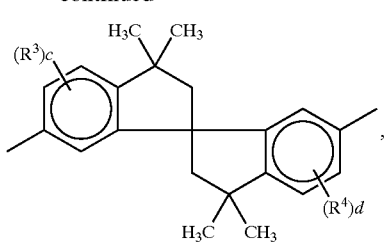

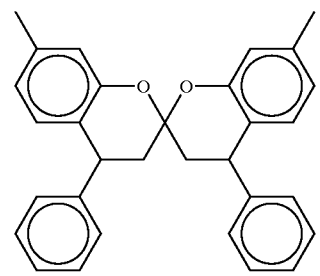

wherein $R^1$, $R^2$, $R^3$ and $R^4$ stand, independently from each other, for an alkyl group, a substituted alkyl group, an aryl group, a substituted aryl group or a halogen atom, a and b are independently an integer of 0–4, c and d are independently an ingeger of 0–3, Y is selected from the group consisting of a direct bond, straight chain alkylene groups having 2–12 carbon atoms, substituted straight chain alkylene groups having 2–12 carbon atoms, branched chain alkylene groups having 3–12 carbon atoms, substituted branched chain alkylene groups having 3–12 carbon atoms, divalent groups composed of at least one alkylene group having 1–10 carbon atoms and at least one —O— or at least one —S—, —O—, —S—, —SO—, —$SO_2$—, —CO—, —COO— and groups represented by the following formulas:

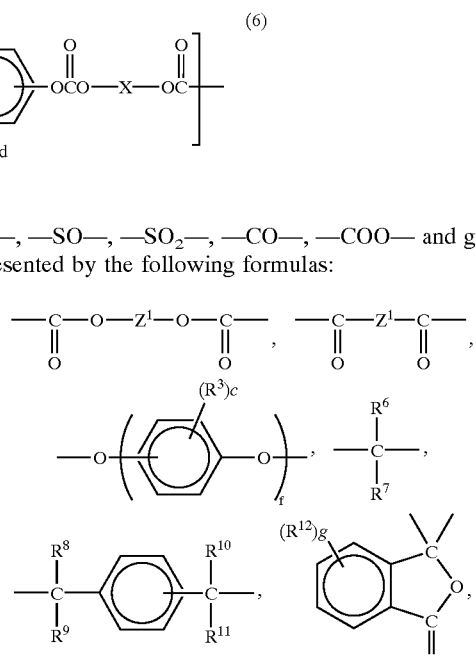

-continued

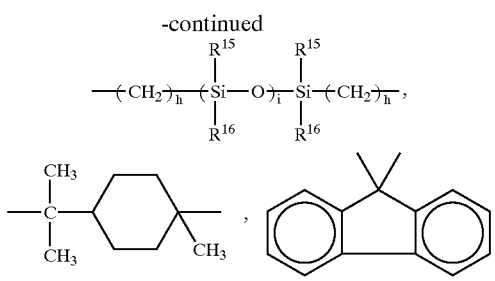

wherein $Z^1$ and $Z^2$ stand independently from each other for a divalent aliphatic group, a substituted divalent aliphatic group, an arylene group or a substituted arylene group; $R^5$, $R^6$ and $R^{12}$ stand independently from each other for a halogen atom, an alkyl group, a substituted alkyl group, an alkoxyl group, a substituted alkoxyl group, an aryl group or a substituted aryl group, $R^7$, $R^8$, $R^9$, $R^{10}$ and $R^{11}$ stand independently from each other for a hydrogen atom, $R^6$ and $R^7$ may form a carbocyclic ring having 5 to 12 carbon atoms together, $R^{13}$ and $R^{14}$ stand independently from each other for a direct bond or an alkylene group having 1–4 carbon atoms, $R^{15}$ and $R^{16}$ stand independently from each other an alkyl group, a substituted alkyl group, an aryl group or a substituted aryl group, e and g are each an integer of 0–4, f is an integer of 1 or 2, h is an integer of 0–20 and i is an integer of 0–2000.

When the above polycarbonate resin according to the present invention is used in a photoconductive layer, problems of the conventional photoconductor in mechanical properties and in electrical properties can be solved. Although not wishing to be bound by the theory, it is presumed that the presence of the aryl-substituted alkane groups through which oxycarbonyl groups of the polycarbonate resin are linked to the aryl groups of the triarylamines can prevent the localization of electrons so that the motion of molecules can be facilitated.

It is an object of the present invention to provide a novel diphenol compound which is useful for producing a novel polycarbonate.

Another object of the present invention is to provide a novel polycarbonate useful as a charge-transporting material for a photoconductive layer of an electrophotographic photoconductor.

It is a further object of the present invention to provide an electrophotographic photoconductor having good mechanical properties as well as good electrical and optical properties such as high photosensitivity and low residual potential.

Other objects, features and advantages of the present invention will become apparent from the detailed description of the preferred embodiments of the invention which follows, when considered in light of the accompanying drawings, in which.

DETAILED DESCRIPTION OF THE PREFERRED EMBODIMENTS OF THE INVENTION

Figure 1:
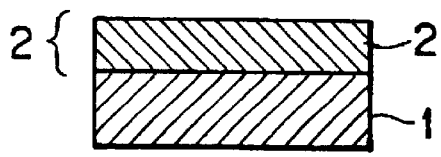
FIG. 1 is a schematic cross-sectional view of a first example of an electrophotographic photoconductor according to the present invention.

An aromatic polycarbonate resin according to the present invention may be produced using a novel diphenol compound of the above formula (1) according to the present invention by any known method such as ester interchange between at least one kind of a diol and a bisarylcarbonate compound, polymerization of a diol with a halogenated carbonyl compound such as phosgene in accordance with solution polymerization or interfacial polymerization, or polymerization using a chloroformate such as bischloroformate derived from a diol.

As the halogenated carbonyl compounds in the above-mentioned polymerization, not only phosgene, but also trichloromethyl chloroformate that is a dimer of phosgene, and bis(trichloromethyl)carbonate that is a trimer of phosgene are usable. Further, halogenated carbonyl compounds derived from other halogen atoms than chlorine, for example, carbonyl bromide, carbonyl iodide and carbonyl fluoride are also employed. Such conventional synthesis methods are described in, for example, "Handbook of Polycarbonate Resin" (edited by HOMMA, Seiichi, published by The Nikkan Kogyo Shimbun Ltd.).

As the diol, a diphenol compound of the formula (2):

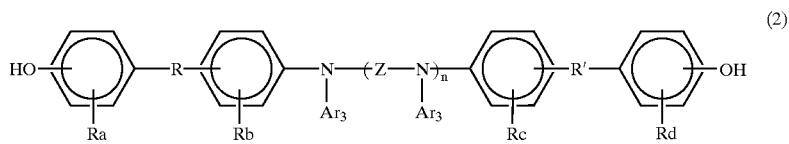

(2)

wherein Ra, Rb, Rc and Rd stand for an alkyl group and $Ar_3$, Z, R, R' and n are the same as those of the formula (1) above, may be suitably used. Further, if desired, for the purpose of improving mechanical properties of the polycarbonate resin, the diphenol of the formula (1) or (2) having a charge transporting property may be used in conjunction with a diol of the formula (7):

(7)

wherein X is the same as that of the formula (6) above. Two or more diols of the formula (7) may be used in combination. The amount of the diol of formula (7) relative to the diol of formula (1) or (2) may be selected within a wide range in light of the desired characteristics of the obtained aromatic polycarbonate resin.

Further, various kinds of copolymers, such as a random copolymer, an alternating copolymer, a block copolymer, a random alternating copolymer, and a random block copolymer can be obtained by appropriately selecting the polymerization procedure. For instance, a random copolymer comprising the structural unit of the above formula (3) or the formula (4) shown below and the structural unit of the formula (5) shown below can be obtained when a uniform mixture containing a diol of formula (1) or (2) with charge transporting properties and a diol of formula (7) is subjected to a condensation reaction with the phosgene:

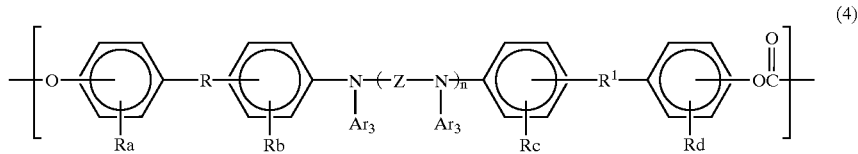

wherein Ra, Rb, Rc, Rd, Ar$_3$, Z, R, R' and n are as defined above,

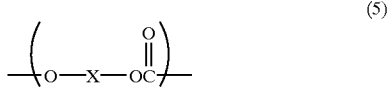

wherein X is as defined above.

A random block copolymer can be obtained by the addition of a plurality of diols in the course of the reaction. Further, an alternating copolymer comprising a repeat unit of the above formula (6) can be produced by carrying out the condensation reaction of a bischloroformate compound derived from the diol of formula (7) and the diol having charge transporting properties, represented by formula (1) or (2). In such a case, the above-mentioned alternating copolymer comprising a repeat unit of formula (6) can be similarly produced by carrying out the condensation reaction of a bischloroformate compound derived from the diol of formula (1) or (2) having charge transporting properties and the diol of formula (7). Further, a random alternating copolymer can be produced by employing a plurality of bischloroformate compounds and/or diol compounds in the course of the aforementioned condensation reaction.

The interfacial polymerization is carried out at the interface between two phases of an alkaline aqueous solution of a diol and an organic solvent which is substantially incompatible with water and capable of dissolving a polycarbonate therein in the presence of the carbonic acid derivative and a catalyst. In this case, a polycarbonate resin with a narrow molecular-weight distribution can be speedily obtained by emulsifying the reactive medium through the high-speed stirring operation or addition of an emulsifying material.

As a base for preparing the alkaline aqueous solution of diol, there can be employed an alkali metal and an alkaline earth metal. Specific examples of the base include hydroxides such as sodium hydroxide, potassium hydroxide and calcium hydroxide; and carbonates such as sodium carbonate, potassium carbonate, calcium carbonate and sodium hydrogencarbonate. Those bases may be used alone or in combination. Of those bases, sodium hydroxide and potassium hydroxide are preferable. In addition, distilled water or deionized water are preferably employed for the preparation of the above-mentioned alkaline aqueous solution of diol.

Examples of the organic solvent used in the above-mentioned interfacial polymerization are aliphatic halogenated hydrocarbon solvents such as dichloromethane, 1,2-dichloroethane, 1,2-dichloroethylene, trichloroethane, tetrachloroethane and dichloropropane; aromatic halogenated hydrocarbon solvents such as chlorobenzene and dichlorobenzene; and mixed solvents thereof. Further, aromatic hydrocarbon solvents such as toluene, xylene and ethylbenzene, or aliphatic hydrocarbon solvents such as hexane and cyclohexane may be added to the above-mentioned solvents. The aliphatic halogenated hydrocarbon solvents and aromatic halogenated hydrocarbon solvents are preferable, and in particular, dichloromethane and chlorobenzene are preferably employed in the present invention.

Examples of the catalyst used in the preparation of the polycarbonate resin include a tertiary amine, a quaternary ammonium salt, a tertiary phosphine, a quaternary phosphonium salt, a nitrogen-containing heterocyclic compound and salts thereof, an iminoether and salts thereof, and a compound having amide group. Specific examples of such catalysts are trimethylamine, triethylamine, tri-n-propylamine, tri-n-hexylamine, N,N,N',N'-tetramethyl-1,4-tetramethylene-diamine, 4-pyrrolidinopyridine, N,N'-dimethylpiperazine, N-ethylpiperidine, benzyltrimethylammonium chloride, benzyltriethylammonium chloride, tetramethylammonium chloride, tetraethylammonium bromide, phenyltriethylammonium chloride, triethylphosphine, triphenylphosphine, diphenylbutylphosphine, tetra(hydroxymethyl) phosphonium chloride, benzyltriethylphosphonium chloride, benzyltriphenylphosphonium chloride, 4-methylpyridine, 1-methylimidazole, 1,2-dimethylimidazole, 3-methylpyridazine, 4,6-dimethylpyrimidine, 1-cyclohexyl-3,5-dimethylpyrazole, and 2,3,5,6-tetramethylpyrazine. Those catalysts may be used alone or in combination. Of the above-mentioned catalysts, the tertiary amine, in particular, a tertiary amine having 3 to 30 carbon atoms, such as triethylamine is preferably employed in the present invention. Before and/or after the carbonic acid derivatives such as phosgene and bischloroformate are placed in the reaction system, any of the above-mentioned catalysts may be added thereto.

To prevent oxidation of the diol in the alkaline aqueous solution in the course of the polymerization reaction, an antioxidant such as hydrosulfite may be used.

The interfacial polymerization reaction is generally carried out at temperature in the range of 0 to 40° C., and terminated in several minutes to 5 hours. It is desirable to maintain the reaction system to pH 10 or more.

In the case of the solution polymerization, the diol is dissolved in a proper solvent to prepare a solution of the diol, and a deacidifying agent is added thereto. Then, the bischloroformate compound, phosgene or the like is added to the above prepared mixture. In this case, tertiary amine compounds such as trimethylamine, triethylamine and tripropylamine, and pyridine can be used as the deacidifying agents. Examples of the solvent for use in the above-mentioned solution polymerization are halogenated hydrocarbon solvents such as dichloromethane, dichloroethane, trichloroethane, tetrachloroethane, trichloroethylene, and chloroform; cyclic ethers such as tetrahydrofuran and dioxane; and pyridine. The reaction temperature is generally in the range of 0 to 40° C. In this case, the solution polymerization is generally terminated in several minutes to 5 hours.

In the case where the polycarbonate resin is synthesized by the ester interchange method, the diol and the bisarylcarbonate are mixed in the presence of an inert gas, and the reaction is carried out at a temperature in the range of 120 to 350° C. under a reduced pressure. The pressure in the reaction system is stepwise reduced up to 1 mmHg or less in order to distill away the phenols generated during the reaction from the reaction system. The reaction is commonly terminated in about one to 4 hours. When necessary, the antioxidant may be added to the reaction system. As the bisarylcarbonate compound, diphenyl carbonate, di-p-tolyl carbonate, phenyl-p-tolyl carbonate, di-p-chlorophenyl carbonate and dinaphthyl carbonate can be employed.

To control the molecular weight of the obtained polycarbonate resin, it is desirable to employ a terminator as a molecular weight modifier in any of the above-mentioned polymerization reactions. Consequently, a substituent derived from the terminator may be bonded to the end of the molecule of the obtained polycarbonate resin.

As the terminator for use in the present invention, a monovalent aromatic hydroxy compound and haloformate derivatives thereof, and a monovalent carboxylic acid and halide derivatives thereof can be used alone or in combination. Specific examples of the monovalent aromatic hydroxy compound are phenols such as phenol, p-cresol, o-ethylphenol, p-ethylphenol, p-isopropylphenol, p-tert-butylphenol, p-cumylphenol, p-cyclohexylphenol, p-octylphenol, p-nonylphenol, 2,4-xylenol, p-methoxyphenol, p-hexyloxyphenol, p-decyloxyphenol, o-chlorophenol, m-chlorophenol, p-chlorophenol, p-bromophenol, pentabromophenol, pentachlorophenol, p-phenylphenol, p-isoprooenylphenol, 2,4-di(1'-methyl-1'-phenylethyl)phenol, β-naphthol, α-naphthol, p-(2',4',4'-trimethylchromanyl)-phenol, and 2-(4'-methoxyphenyl)-2-(4''-hydroxyphenyl)-propane. In addition, alkali metal salts and alkaline earth metal salts of the above phenols can also be employed. Various haloformate derivatives of the above-mentioned aromatic hydroxy compounds can be used as the terminators.

Specific examples of the monovalent carboxylic acid are aliphatic acids such as acetic acid, propionic acid, butyric acid, valeric acid, caproic acid, heptanic acid, caprylic acid, 2,2-dimethylpropionic acid, 3-methylbutyric acid, 3,3-dimethylbutyric acid, 4-methylvaleric acid, 3,3-dimethylvaleric acid, 4-methylcaproic acid, 3,5-dimethylcaproic acid and phenoxyacetic acid; and benzoic acids such as benzoic acid, p-methylbenzoic acid, p-tert-butylbenzoic acid, p-butoxybenzoic acid, p-octyloxybenzoic acid, p-phenylbenzoic acid, p-benzylbenzoic acid and p-chlorobenzoic acid. In addition, alkali metal salts and alkaline earth metal salts of the above-mentioned aliphatic acids and benzoic acids can also be employed. In addition, various halide derivatives of the above-mentioned monovalent carboxylic acids can be employed as the terminators. The above terminators may be used singly or in combination of two or more. A monovalent aromatic hydroxy compound, in particular phenol, p-tert-butylphenol or p-cumylphenol is especially preferably used for the purpose of the present invention.

Furthermore, a branching agent may be added in a small amount during the polymerization reaction in order to improve the mechanical properties of the obtained polycarbonate resin. Any compounds that have three or more reactive groups, which may be the same or different, selected from the group consisting of an aromatic hydroxyl group, a haloformate group, a carboxylic acid group, a carboxylic acid halide group, and an active halogen atom can be used as the branching agents for use in the present invention.

Specific examples of the branching agents for use in the present invention are as follows: phloroglucinol,
4,6-dimethyl-2,4,6-tris(4'-hydroxyphenyl)-2-heptene,
4,6-dimethyl-2,4,6-tris(4'-hydroxyphenyl)heptane,
1,3,5-tris(4'-hydroxyphenyl)benzene,
1,1,1-tris(4'-hydroxyphenyl)ethane,
1,1,2-tris(4'-hydroxyphenyl)propane,
α,α,α'-tris(4'-hydroxyphenyl)-1-ethyl-4-isopropylbenzene,
2,4-bis[α-methyl-α-(4'-hydroxyphenyl)ethyl]phenol,
2-(4'-hydroxyphenyl)-2-(2'',4''-dihydroxyphenyl)-propane,
tris(4-hydroxyphenyl)phosphine,
1,1,4,4-tetrakis(4'-hydroxyphenyl)cyclohexane,
2,2-bis[4',4'-bis(4''-hydroxyphenyl)cyclohexyl]-propane,
α,α',α,α'-tetrakis(4'-hydroxyphenyl)-1,4-diethylbenzene,
2,2,5,5-tetrakis(4'-hydroxyphenyl)hexane,
1,1,2,3-tetrakis(4'-hydroxyphenyl)propane,
1,4-bis(4',4''-dihydroxytriphenylmethyl)benzene,
3,3',5,5'-tetrahydroxydiphenyl ether,
3,5-dihydroxybenzoic acid,
3,5-bis(chlorocarbonyloxy)benzoic acid,
4-hydroxyisophthalic acid,
4-chlorocarbonyloxyisophthalic acid,
5-hydroxyphthalic acid,
5-chlorocarbonyloxyphthalic acid,
trimesic trichloride, and
cyanuric chloride.

Those branching agents may be used alone or in combination.

The polycarbonate resin thus prepared is purified by removing the catalyst and the anti-oxidation agent used in the polymerization; unreacted diol and terminator; and impurities such as an inorganic salt generated during the polymerization. Methods for purifying the polycarbonate resin are disclosed in previously mentioned "Handbook of Polycarbonate Resin" (issued by Nikkan Kogyo Shimbun Ltd.). In the present invention, it is preferable that the aromatic polycarbonate resin thus obtained have a number-average molecular weight of 1,000 to 500,000, more preferably in the range of 10,000 to 200,000 when expressed in terms of a number-average molecular weight of polystyrene.

If desired, various additives such as an antioxidant, a light stabilizer, a thermal stabilizer, a lubricant and a plasticizer can be added to the aromatic polycarbonate resin produced by the previously mentioned methods.

The diphenol compound represented by the above formula (1) or (2) will be next explained in more detail. In the formulas (1) and (2), $Ar_3$ represents an aryl group or a substituted aryl group. Examples of the aryl group include phenyl group, naphthyl group, biphenylyl group, terphenylyl group, pyrenyl group, fluorenyl group, 9,9-dimethyl-2-fluorenyl group, azulenyl group, anthryl group, triphenylenyl group, chrysenyl group, fluorenylidenephenyl group, 5H-dibenzo[a,d]cyclo-heptenylidenephenyl group, thienyl group, benzothienyl group, furyl group, benzofuranyl group, carbazolyl group, pyridinyl group, pyrrolidyl group, and oxazolyl group. The above-mentioned aryl group may have one or more substituents such as a substituted or unsubstituted alkyl group, a substituted or unsubstituted alkoxyl group, a halogen atom such as fluorine atom, chlorine atom, bromine atom or iodine atom, or an amino group represented by the formula

—N(R$^{17}$)(R$^{18}$)

where R$^{17}$ and R$^{18}$ are independently a substituted or unsubstituted alkyl group or such a substituted or unsubstituted aryl group as defined in connection with Ar$^3$, and R$^{17}$ and R$^{18}$ may form a ring or a fused ring such as piperidino group, morpholino group or julolidyl group.

In the formulas (1) and (2), Ar$_1$, Ar$_2$, Ar$_4$ and Ar$_5$ are independently an arylene group or a substituted arylene group such as derived from Ar$_3$. The arylene group Z may be, for example, phenylene, naphthylene, biphenylene, terphenylene, pyrene-1,6-diyl, fluorene-2,7-diyl, 9,9-dimethylfluorene-2,7-diyl, thiophene-2,5-diyl, furan-2,5-diyo, N-ethylcarbazole-3,6-diyl. These arylene groups may have one or more substituents such as alkyl, substituted alkyl, alkoxyl, substituted alkoxyl and a halogen atom. The arylene group Ar$_6$ of Z may be, for example, phenylene, naphthylene, biphenylene, or terphenylene, each of which may have one or more substituents such as alkyl, substituted alkyl, alkoxyl, substituted alkoxyl and a halogen atom.

The groups Ra, Rb, Rc and Rd of the formula (2) are each an alkyl group or a substituted alkyl group. The alkyl group is preferably straight chain or branched chain alkyl having 1–5 carbon atoms. The substituent may be a halogen atom, a cyano group, a phenyl group or a substituted phenyl group. The substituent of the phenyl group may be a halogen atom or straight chain or branched chain alkyl having 1–5 carbon atoms. Specific examples of Ra, Rb, Rc and Rd include methyl, ethyl, n-propyl, i-propyl, t-butyl, s-butyl, n-butyl, i-butyl, trifluoromethyl, 2-cyanoethyl, benzyl, 4-chlorobenzyl and 4-methylbenzyl.

The diphenol compound of the formula (1) above may be prepared according to the following scheme (in the following description X' and R" represent a halogen atom and a lower alkyl group, respectively.

Scheme 1

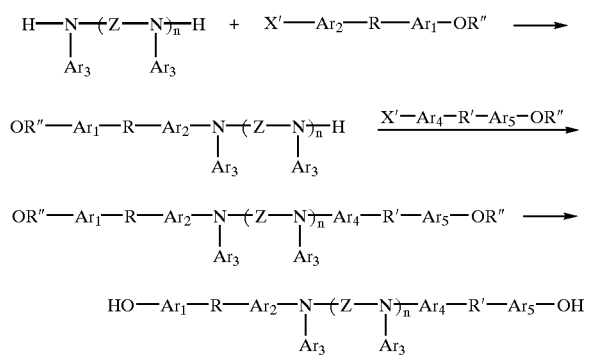

In Scheme 1, a dialkoxyl compound obtained by Ulmann reaction between a secondary amine with a halogen compound is subjected to an ether linkage cleaving reaction, thereby to yield the diphenol. It is without saying that, when Ar$_1$, Ar$_2$ and R are the same as Ar$_5$, Ar$_4$ and R', respectively, the dialkoxyl compound is produced by one stage.

Scheme 2

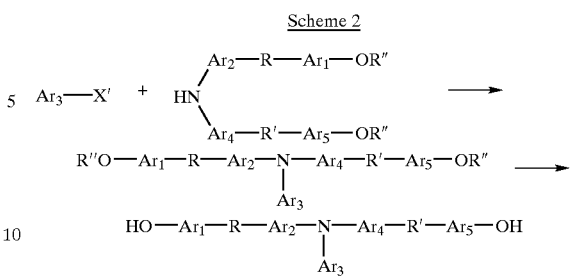

Scheme 2 represents a case where n of the diphenol compound of the formula (1) is 0. In this scheme too, the diphenol compound is produced by the Ulmann reaction followed by the ether linkage cleaving reaction.

Scheme 3

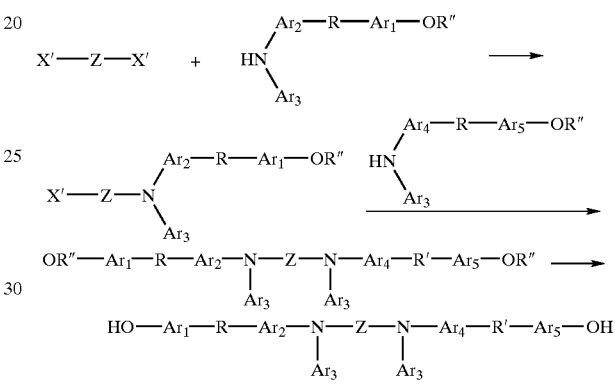

Scheme 3 represents a case where n of the diphenol compound of the formula (1) is 1. In this scheme too, the diphenol compound is produced by the Ulmann reaction followed by the ether linkage cleaving reaction. It is without saying that, when Ar$_1$, Ar$_2$ and R are the same as Ar$_5$, Ar$_4$ and R', respectively, the dialkoxyl compound is produced by one stage.

Scheme 4

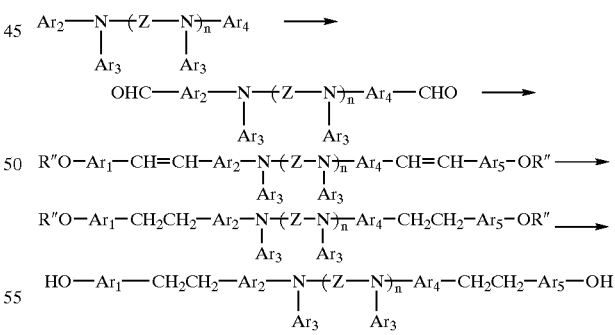

Scheme 4 represents a case in which R and R' of the diphenol compound of the formula (1) are ethylene. A tertiary amine is diformylated, which is then converted into a diolefin compound by a modified Wittig reaction. The diolefin compound is then reduced and subjected to ether linkage cleaving reaction, thereby obtaining the diphenol compound.

The ether linkage cleaving reaction may be carried out by using an acidic reagent such as hydrogen bromide, hydrogen iodide, trifluoroacetic acid, hydrochloric acid salt of pyridine, concentrated hydrochloric acid, magnesium iodide ethylate, aluminum chloride, aluminum bromide, boron tribromide, boron trichloride or boron triiodide; or a basic reagent such as potassium hydroxide, sodium hydroxide, sodium, lithium, sodium iodide, lithium diphenylphosphide or sodium thiolate. The reaction may be performed in the presence of a solvent such as acetic anhydride, dichloromethane, tetrahydrofuran, dimethylformamide, pyridine, toluene or butanol. The reaction temperature is generally −10° C. to 200° C.

The diphenol compound of the formula (1) and (2) is a novel compound and is useful as a monomer for preparing various polymers such as a polycarbonate resin, a polyester resin, a polyurethane resin and an epoxy resin.

In the case where X of formula (7) represents a bivalent aliphatic group or a bivalent cyclic aliphatic group, the representative examples of the diol are as follows: ethylene glycol, diethylene glycol, triethylene glycol, polyethylene glycol, polytetramethylene ether glycol, 1,3-propanediol, 1,4-butanediol, 1,5-pentanediol, 3-methyl-1,5-pentanediol, 1,6-hexanediol, 1,5-hexanediol, 1,7-heptanediol, 1,8-octanediol, 1,9-nonanediol, 1,10-decanediol, 1,11-undecanediol, 1,12-dodecanediol, neopentyl glycol, 2-ethyl-1,6-hexanediol, 2-methyl-1,3-propanediol, 2-ethyl-1,3-propanediol, 2,2-dimethyl-1,3-propanediol, 1,3-cyclohexanediol, 1,4-cyclohexanediol, cyclohexane-1,4-dimethanol, 2,2-bis(4-hydroxycyclohexyl)propane, xylylenediol, 1,4-bis(2-hydroxyethyl)benzene, 1,4-bis(3-hydroxypropyl)benzene, 1,4-bis(4-hydroxybutyl)benzene, 1,4-bis(5-hydroxypentyl)benzene, 1,4-bis(6-hydroxyhexyl) benzene and isophoronediol.

In the case where X of formulas (5)–(7) represents a bivalent aromatic group, there can be employed any bivalent groups derived from such a substituted or unsubstituted aryl group as defined in the description of $Ar_3$. In addition, X represents a bivalent group selected from the following groups:

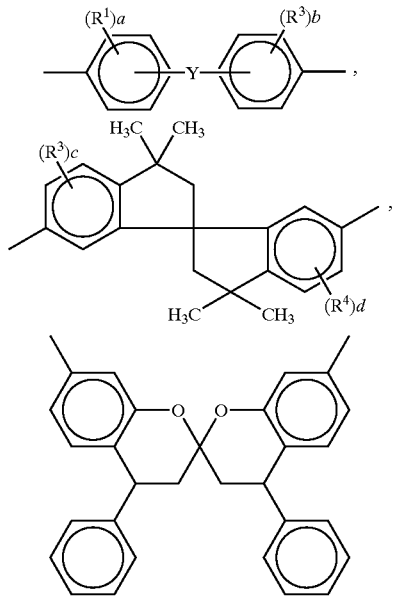

wherein $R^1$, $R^2$, $R^3$ and $R^4$ stand, independently from each other, for an alkyl group, a substituted alkyl group, an aryl group, a substituted aryl group or a halogen atom, a and b are independently an integer of 0–4, c and d are independently an ingeger of 0–3, Y is selected from the group consisting of a direct bond, straight chain alkylene groups having 2–12 carbon atoms, substituted straight chain alkylene groups having 2–12 carbon atoms, branched chain alkylene groups having 3–12 carbon atoms, substituted branched chain alkylene groups having 3–12 carbon atoms, divalent groups composed of at least one alkylene group having 1–10 carbon atoms and at least one —O— or at least one —S—, —O—, —S—, —SO—, —SO$_2$—, —CO—, —COO— and groups represented by the following formulas:

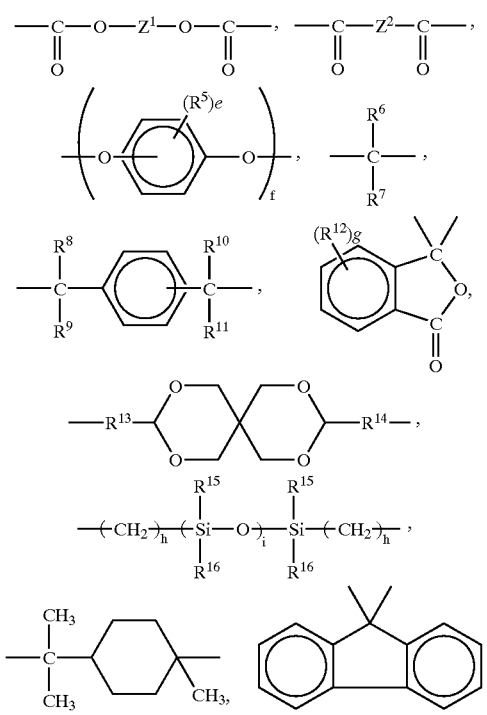

wherein $Z^1$ and $Z^2$ stand independently from each other for a divalent aliphatic group, a substituted divalent aliphatic group, an arylene group or a substituted arylene group; $R^5$, $R^6$ and $R^{12}$ stand independently from each other for a halogen atom, an alkyl group, a substituted alkyl group, an alkoxyl group, a substituted alkoxyl group, an aryl group or a substituted aryl group, $R^7$, $R^8$, $R^9$, $R^{10}$ and $R^{11}$ stand independently from each other for a hydrogen atom, $R^6$ and $R^7$ may form a carbocyclic ring having 5 to 12 carbon atoms together, $R^{13}$ and $R^{14}$ stand independently from each other for a direct bond or an alkylene group having 1–4 carbon atoms, $R^{15}$ and $R^{16}$ stand independently from each other an alkyl group, a substituted alkyl group, an aryl group or a substituted aryl group, e and g are each an integer of 0–4, f is an integer of 1 or 2, h is an integer of 0–20 and i is an integer of 0–2000.

Examples of the bivalent group Y having at least one alkylene group having 1 to 10 carbon atoms and at least one oxygen atom and/or sulfur atom include:
OCH$_2$CH$_2$O,
OCH$_2$CH$_2$OCH$_2$CH$_2$O
OCH$_2$CH$_2$OCH$_2$CH$_2$OCH$_2$CH$_2$O
OCH$_2$CH$_2$CH$_2$O
OCH$_2$CH$_2$CH$_2$CH$_2$O
OCH$_2$CH$_2$CH$_2$CH$_2$CH$_2$CH$_2$O
OCH$_2$CH$_2$CH$_2$CH$_2$CH$_2$CH$_2$CH$_2$CH$_2$O
CH$_2$O
CH$_2$CH$_2$O
CH(C$_2$H$_5$)OCH(C$_2$H$_5$)O
CHCH$_3$O SCH₂OCH₂S
CH₂OCH₂
OCH₂OCH₂O
SCH₂CH₂OCH₂OCH₂CH₂S
OCH₂CHCH₃OCH₂CHCH₃O
SCH₂S
SCH₂CH₂S
SCH₂CH₂CH₂S
SCH₂CH₂CH₂CH₂S
SCH₂CH₂CH₂CH₂CH₂CH₂S
SCH₂CH₉SCH₂CH₂S
SCH₂CH₂OCH₂CH₂OCH₂CH₂S The substituents for Y of the branched chain alkylene groups having 3–12 carbon atoms may be an aryl group, a substituted aryl group or a halogen atom. In the definition of X, the substituted or unsubstituted alkyl or aryl may be the same as those described previously.

When $Z_1$ and $Z_2$ each represent a substituted or unsubstituted bivalent aliphatic group, there can be employed any bivalent groups obtained by removing the hydroxyl groups from the diol of formula (7) in which X represents a bivalent aliphatic group or a bivalent cyclic aliphatic group. On the other hand, when $Z_1$ and $Z_2$ each represent a substituted or unsubstituted arylene group, there can be employed any bivalent groups derived from the substituted or unsubstituted aryl group as defined in the description of $Ar_3$.

Preferable examples of the diol of formula (7) in which X represents a bivalent aromatic group are as follows:
bis(4-hydroxyphenyl)methane,
bis(2-methyl-4-hydroxyphenyl)methane,
bis(3-methyl-4-hydroxyphenyl)methane,
1,1-bis(4-hydroxyphenyl)ethane,
1,2-bis(4-hydroxyphenyl)ethane,
bis(4-hydroxyphenyl)phenylmethane,
bis(4-hydroxyphenyl)diphenylmethane,
1,1-bis(4-hydroxyphenyl)-1-phenylethane,
1,3-bis(4-hydroxyphenyl)-1,1-dimethylpropane,
2,2-bis(4-hydroxyphenyl)propane,
2-(4-hydroxyphenyl)-2-(3-hydroxyphenyl)propane,
1,1-bis(4-hydroxyphenyl)-2-methylpropane,
2,2-bis(4-hydroxyphenyl)butane,
1,1-bis(4-hydroxyphenyl)-3-methylbutane,
2,2-bis(4-hydroxyphenyl)pentane,
2,2-bis(4-hydroxyphenyl)-4-methylpentane,
2,2-bis(4-hydroxyphenyl)hexane,
4,4-bis(4-hydroxyphenyl)heptane,
2,2-bis(4-hydroxyphenyl)nonane,
bis(3,5-dimethyl-4-hydroxyphenyl)methane,
2,2-bis(3-methyl-4-hydroxyphenyl)propane,
2,2-bis(3-isopropyl-4-hydroxyphenyl)propane,
2,2-bis(3-sec-butyl-4-hydroxyphenyl)propane,
2,2-bis(3-tert-butyl-4-hydroxyphenyl)propane,
2,2-bis(3-cyclohexyl-4-hydroxyphenyl)propane,
2,2-bis(3-allyl-4-hydroxyphenyl)propane,
2,2-bis(3-phenyl-4-hydroxyphenyl)propane,
2,2-bis(3,5-dimethyl-4-hydroxyphenyl)propane,
2,2-bis(3-chloro-4-hydroxyphenyl)propane,
2,2-bis(3,5-dichloro-4-hydroxyphenyl)propane,
2,2-bis(3-bromo-4-hydroxyphenyl)propane,
2,2-bis(3,5-dibromo-4-hydroxyphenyl)propane,
2,2-bis(4-hydroxyphenyl)hexafluoropropane,
1,1-bis(4-hydroxyphenyl)cyclopentane,
1,1-bis(4-hydroxyphenyl)cyclohexane,
1,1-bis(3-methyl-4-hydroxyphenyl)cyclohexane,
1,1-bis(3,5-dimethyl-4-hydroxyphenyl)cyclohexane,
1,1-bis(3,5-dichloro-4-hydroxyphenyl)cyclohexane,
1,1-bis(4-hydroxyphenyl)-3,3,5-trimethylcyclohexane,
1,1-bis(4-hydroxyphenyl)cycloheptane,
2,2-bis(4-hydroxyphenyl)norbornane,
2,2-bis(4-hydroxyphenyl)adamantane,
4,4'-dihydroxydiphenyl ether,
4,4'-dihydroxy-3,3'-dimethyldiphenyl ether,
ethylene glycol bis(4-hydroxyphenyl)ether,
4,4'-dihydroxydiphenylsulfide,
3,3'-dimethyl-4,4'-dihydroxydiphenylsulfide,
3,3',5,5'-tetramethyl-4,4'-dihydroxydiphenylsulfide,
4,4'-dihydroxydiphenylsulfoxide,
3,3'-dimethyl-4,4'-dihydroxydiphenylsulfoxide,
4,4'-dihydroxydiphenylsulfone,
3,3'-dihyhydroxydiphenylsulfone,
3,3'-diphenyl-4,4'-dihydroxydiphenylsulfone,
3,3'-dichloro-4,4'-dihydroxydiphenylsulfone,
bis(4-hydroxyphenyl)ketone,
bis(3-methyl-4-hydroxyphenyl)ketone,
3,3,3',3'-tetramethyl-6,6'-dihydroxyspiro(bis)-indane,
3,3',4,4'-tetrahydro-4,4,4',4'-tetramethyl-2,2'-spirobi(2H-1-benzopyrane)-7,7'-diol,
trans-2,3-bis(4-hydroxyphenyl)-2-butene,
9,9-bis(4-hydroxyphenyl)fluorene,
9,9-bis(4-hydroxyphenyl)xanthene,
1,6-bis(4-hydroxyphenyl)-1,6-hexanedione,
α.α,α',α'-tetramethyl-α,α'-bis(4-hydroxyphenyl)-p-xylene,
α,α,α',α'-tetramethyl-α,α'-bis(4-hydroxyphenyl)-m-xylene,
2,6-dihydroxydibenzo-p-dioxine,
2,6-dihydroxythianthrene,
2,7-dihydroxyphenoxathine,
9,10-dimethyl-2,7-dihydroxyphenazine,
3,6-dihydroxydibenzofuran,
3,6-dihydroxydibenzothiophene,
4,4'-dihydroxybiphenyl,
1,4-dihydroxynaphthalene,
2,7-dihydroxypyrene,
hydroquinone,
resorcin,
ethylene glycol-bis(4-hydroxybenzoate),
diethylene glycol-bis(4-hydroxybenzoate),
triethylene glycol-bis(4-hydroxybenzoate),
1,13-bis(4-hydroxyphenyl)-tetramethyldisiloxane, and phenol-modified silicone oil. Further, an aromatic diol having an ester linkage produced by the reaction between 2 moles of a diol and one mole of isophthaloyl chloride or terephthaloyl chloride is also usable.

The above explanation of X for the diol of the formula (7) also applies to X of the formulas (5) and (6).

The novel polycarbonate resin according to the present invention is suitably used for electrophotographic photoconductors. Explanation will now be made of embodiments shown in FIGS. 1 through 6 in which the polycarbonate resin is contained in photoconductive layers 2, 2a, 2b, 2c, 2d, and 2e.

In the photoconductor shown in FIG. 1, a photoconductive layer 2 is formed on an electroconductive support 1, which photoconductive layer 2 comprises the previously mentioned aromatic polycarbonate resin according to the present invention and a sensitizing dye, with the addition thereto of a binder agent (binder resin) when necessary. In this photoconductor, the aromatic polycarbonate resin works as a photoconductive material, through which charge carriers necessary for the light decay of the photoconductor are generated and transported. However, the aromatic polycarbonate resin itself scarcely absorbs light in the visible light range and, therefore, it is necessary to add a sensitizing dye which absorbs light in the visible light range in order to form latent electrostatic images by use of visible light.

Figure 2:
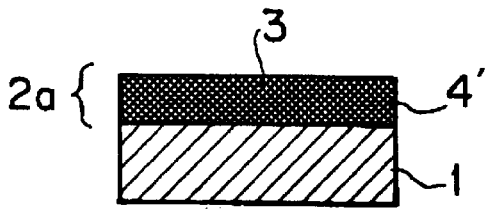
FIG. 2 is a schematic cross-sectional view of a second example of an electrophotographic photoconductor according to the present invention.

Referring to FIG. 2, there is shown an enlarged cross-sectional view of another embodiment of an electrophotographic photoconductor according to the present invention. In this photoconductor, there is formed a photoconductive layer 2a on an electroconductive support 1. The photoconductive layer 2a comprises a charge transport medium 4' comprising (i) an aromatic polycarbonate resin having charge transporting properties according to the present invention, optionally in combination with a binder agent, and (ii) a charge generation material 3 dispersed in the charge transport medium 4'. In this embodiment, the aromatic polycarbonate resin (or a mixture of the aromatic polycarbonate resin and the binder agent) constitutes the charge transport medium 4'. The charge generation material 3, which is, for example, an inorganic material or an organic pigment, generates charge carriers. The charge transport medium 4' accepts the charge carriers generated by the charge generation material 3 and transports those charge carriers. In this electrophotographic photoconductor of FIG. 2, it is basically necessary that the light-absorption wavelength regions of the charge generation material 3 and the aromatic polycarbonate resin not overlap in the visible light range. This is because, in order that the charge generation material 3 produce charge carriers efficiently, it is necessary that light pass through the charge transport medium 4' and reach the surface of the charge generation material 3. Since the aromatic polycarbonate resin of the present invention do not substantially absorb light with a wavelength of 600 nm or more, it can work effectively as a charge transport material when used with the charge generation material 3 which absorbs the light in the visible region to the near infrared region and generates charge carriers. The charge transport medium 4' may further comprise the previously mentioned low-molecular weight charge transport material.

Figure 3:
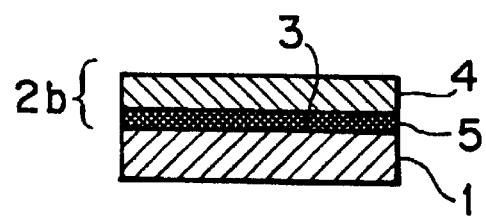
FIG. 3 is a schematic cross-sectional view of a third example of an electrophotographic photoconductor according to the present invention.

Referring to FIG. 3, there is shown an enlarged cross-sectional view of a further embodiment of an electrophotographic photoconductor according to the present invention. In the figure, there is formed on an electroconductive support 1 a two-layered photoconductive layer 2b comprising a charge generation layer 5 containing a charge generation material 3, and a charge transport layer 4 comprising an aromatic polycarbonate resin with the charge transporting properties according to the present invention. In this photoconductor, light which has passed through the charge transport layer 4 reaches the charge generation layer 5, and charge carriers are generated within the charge generation layer 5. The charge carriers which are necessary for the light decay for latent electrostatic image formation are generated by the charge generation material 3, and accepted and transported by the charge transport layer 4. The generation and transportation of the charge carriers are performed by the same mechanism as that in the photoconductor shown in FIG. 2.

In this case, the charge transport layer 4 comprises the aromatic polycarbonate resin with charge transporting properties, optionally in combination with a binder agent. Furthermore, in order to increase the efficiency of generating the charge carriers, the charge generation layer 5 may further comprise the above-mentioned aromatic polycarbonate resin, and the photoconductive layer 2b including the charge generation layer 5 and the charge transport layer 4 may further comprise the previously mentioned low-molecular weight charge transport material. This can be applied to the embodiments of FIGS. 4 to 6 to be described later.

Figure 4:
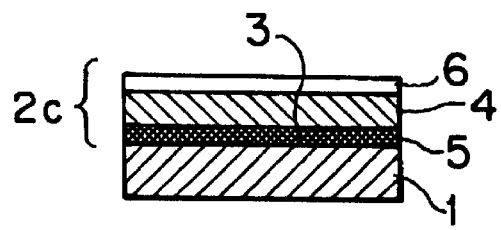
FIG. 4 is a schematic cross-sectional view of a fourth example of an electrophotographic photoconductor according to the present invention.

In the electrophotographic photoconductor of FIG. 4, a protective layer 6 is provided on the charge transport layer 4 as shown in FIG. 4. The protective layer 6 may comprise the aromatic polycarbonate resin of the present invention, optionally in combination with a binder agent. In such a case, it is effective that the protective layer 6 be provided on a charge transport layer in which a low-molecular weight charge transport material is dispersed. The protective layer 6 may be provided on the photoconductive layer 2a of the photoconductor shown in FIG. 2.

Figure 5:
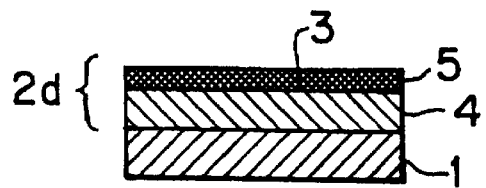
FIG. 5 is a schematic cross-sectional view of a fifth example of an electrophotographic photoconductor according to the present invention.

Referring to FIG. 5, there is shown still another embodiment of an electrophotographic photoconductor according to the present invention. In this figure, the overlaying order of the charge generation layer 5 and the charge transport layer 4 comprising the aromatic polycarbonate resin is reversed in view of the electrophotographic photoconductor as shown in FIG. 3. The mechanism of the generation and transportation of charge carriers is substantially the same as that of the photoconductor shown in FIG. 3.

Figure 6:
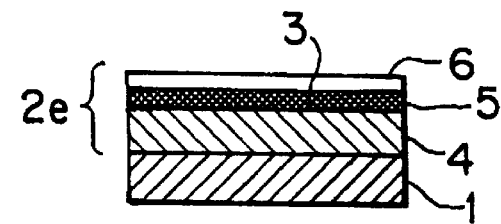
FIG. 6 is a schematic cross-sectional view of a sixth example of an electrophotographic photoconductor according to the present invention.

In the above photoconductor of FIG. 5, a protective layer 6 may be formed on the charge generation layer 5 as shown in FIG. 6 in light of the mechanical strength of the photoconductor.

When the electrophotographic photoconductor according to the present invention shown in FIG. 1 is fabricated, at least one aromatic polycarbonate resin with charge transporting properties is dissolved in a solvent, with the addition thereto of a binder agent when necessary. To the thus prepared solution, a sensitizing dye is added, so that a coating liquid for the photoconductive layer 2 is prepared. The thus prepared photoconductive layer coating liquid is coated on an electroconductive support 1 and dried, so that a photoconductive layer 2 is formed on the electroconductive support 1.

It is preferable that the thickness of the photo-conductive layer 2 be in the range of 3 to 50 $\mu$m, more preferably in the range of 5 to 40 $\mu$m. It is preferable that the amount of aromatic polycarbonate resin with charge transporting properties be in the range of 30 to 100 wt. % of the total weight of the photoconductive layer 2. It is preferable that the amount of sensitizing dye for use in the photoconductive layer 2 be in the range of 0.1 to 5 wt. %, more preferably in the range of 0.5 to 3 wt. % of the total weight of the photoconductive layer 2.

Specific examples of the sensitizing dye for use in the present invention are triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; and cyanine dyes such as cyanin.

The electrophotographic photoconductor shown in FIG. 2 can be produced by the following method: The finely-divided particles of the charge generation material 3 are dispersed in a solution in which at least one aromatic polycarbonate resin with charge transporting properties, or a mixture of the aromatic polycarbonate resin and the binder agent is dissolved, so that a coating liquid for the photoconductive layer 2a is prepared. The coating liquid thus prepared is coated on the electroconductive support 1 and then dried, whereby the photoconductive layer 2a is provided on the electroconductive support 1.

It is preferable that the thickness of the photo-conductive layer 2a be in the range of 3 to 50 $\mu$m, more preferably in the range of 5 to 40 $\mu$m. It is preferable that the amount of aromatic polycarbonate resin with charge transporting properties be in the range of 40 to 100 wt. % of the total weight of the photoconductive layer 2a. It is preferable that the amount of charge generation material 3 for use in the photoconductive layer 2a be in the range of 0.1 to 50 wt. %, more preferably in the range of 1 to 20 wt. % of the total weight of the photoconductive layer 2a.

Specific examples of the charge generation material 3 for use in the present invention are as follows: inorganic materials such as selenium, selenium-tellurium, cadmium sulfide, cadmium sulfide-selenium and .alpha.-silicon (amorphous silicon) and organic pigments, for example, azo pigments, such as C.I. Pigment Blue 25 (C.I. 21180), C.I. Pigment Red 41 (C.I. 21200), C.I. Acid Red 52 (C.I. 45100), C.I. Basic Red 3 (C.I. 45210), an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); phthalocyanine pigments such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B and Indanthrene Scarlet R (made by Bayer Co., Ltd.). These charge generation materials may be used alone or in combination.

When the above-mentioned charge generation material comprises a phthalocyanine pigment, the sensitivity and durability of the obtained photoconductor are remarkably improved, in such a case, there can be employed a phthalocyanine pigment having a phthalocyanine skeleton as indicated by the following formula:

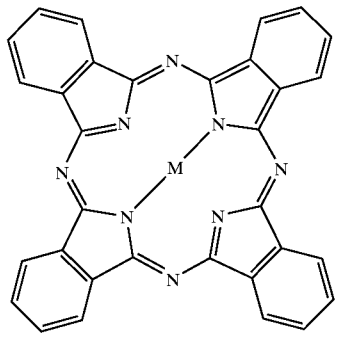

wherein M (central atom) is a metal atom or hydrogen atom.

To be more specific, as the central atom (M) in the above formula, there can be employed an atom of H, Li, Be, Na, Mg, Al, Si, K, Ca, Sc, Ti, V, Cr, Mn, Fe, Co, Ni, Cu, Zn, Ga, Ge, Y, Zr, Nb, Mo, Tc, Ru, Rh, Pd, Ag, Cd, In, Sn, Sb, Ba, Hf, Ta, W, Re, Os, Ir, Pt, Au, Hg, Tl, La, Ce, Pr, Nd, Pm, Sm, Eu, Gd, Tb, Dy, Ho, Er, Tm, Yb, Lu, Th, Pa, U, Np or Am; the combination of atoms forming an oxide, chloride, fluoride, hydroxide or bromide. The central atom is not limited to the above-mentioned atoms.

The above-mentioned charge generation material with a phthalocyanine structure for use in the present invention may have at least the basic structure as indicated by the above-mentioned formula. Therefore, the charge generation material may have a dimer structure or trimer structure, and further, a polymeric structure. Further, the above-mentioned basic structure of the above formula (16) may have a substituent.

Of the phthalocyanine compounds represented by formula (16), an oxotitanium phthalocyanine compound which has the central atom (M) of TiO in the formula (16) and a metal-free phthalocyanine compound which has a hydrogen atom as the central atom (M) are particularly preferred in the present invention because the obtained photoconductors show excellent photoconductive properties. In addition, it is known that each phthalocyanine compound has a variety of crystal systems. For example, the above-mentioned oxotitanium phthalocyanine has crystal systems of α-type, β-type, γ-type, m-type, and y-type. In the case of copper phthalocyanine, there are crystal systems of α-type, β-type, and γ-type. The properties of the phthalocyanine compound vary depending on the crystal system thereof although the central metal atom is the same. According to "Electrophotography—the Society Journal—Vol. 29, No. 4 (1990)", it is reported that the properties of the photoconductor vary depending on the crystal system of a phthalocyanine contained in the photoconductor. In light of the desired photoconductive properties, therefore, it is important to employ the phthalocyanine compounds each having the optimal crystal system. The oxotitanium phthalocyanine in the y-type crystal system is particularly advantageous.

The above-described charge generating materials having a phthalocyanine skeleton may be used singly or in combination of two or more, or in conjunction with other charge generating materials having no phthalocyanine skelenton, such as inorganic charge generating materials and organic charge generating materials.

The electrophotographic photoconductor shown in FIG. 3 can be produced by the following method:

To provide the charge generation layer 5 on the electroconductive support 1, the charge generation material is vacuum-deposited on the electroconductive support 1. Alternatively, the finely-divided particles of the charge generation material 3 are dispersed in an appropriate solvent, together with the binder agent when necessary, so that a coating liquid for the charge generation layer 5 is prepared. The thus prepared coating liquid is coated on the electroconductive support 1 and dried, whereby the charge generation layer 5 is formed on the electroconductive support 1. The charge generation layer 5 may be subjected to surface treatment by buffing and adjustment of the thickness thereof if required. On the thus formed charge generation layer 5, a coating liquid in which at least one aromatic polycarbonate resin with charge transporting properties, optionally in combination with a binder agent, is dissolved is coated and dried, so that the charge transport layer 4 is formed on the charge generation layer 5. In the charge generation layer 5, the same charge generation materials as employed in the above-mentioned photoconductive layer 2a can be used.

The thickness of the charge generation layer 5 is generally 5 μm or less, preferably 2 μm or less. It is preferable that the thickness of the charge transport layer 4 be in the range of 3 to 50 μm, more preferably in the range of 5 to 40 μm. When the charge generation layer 5 is provided on the electroconductive support 1 by coating the dispersion in which finely-divided particles of the charge generation material 3 are dispersed in an appropriate solvent, it is preferable that the amount of finely-divided particles of the charge generation material 3 for use in the charge generation layer 5 be in the range of 10 to 100 wt. %, more preferably in the range of about 50 to 100 wt. % of the total weight of the charge generation layer 5. It is preferable that the amount of aromatic polycarbonate resin of the present invention 4 be in the range of 40 to 100 wt. % of the total weight of the charge transport layer 4.

The photoconductive layer 2b of the photoconductor shown in FIG. 3 may comprise a low-molecular-weight charge transport material. Specific examples of the low-molecular weight charge-transport materials are as follows: oxazole derivatives, oxadiazole derivatives (Japanese Laid-Open Patent Applications 52-139065 and 52-139066), imidazole derivatives, triphenylamine derivatives (Japanese Laid-Open Patent Application 3-285960), benzidine derivatives (Japanese Patent Publication 58-32372), α-phenylstilbene derivatives (Japanese Laid-Open Patent Application 57-73075), hydrazone derivatives (Japanese Laid-Open Patent Applications 55-154955, 55-156954, 55-52063, and 56-81850), triphenylmethane derivatives (Japanese Patent Publication 51-10983), anthracene derivatives (Japanese Laid-Open Patent Application 51-94829), styryl derivatives (Japanese Laid-Open Patent Applications 56-29245 and 58-198043), carbazole derivatives (Japanese Laid-Open Patent Application 58-58552), and pyrene derivatives (Japanese Laid-Open Patent Application 2-94812).

To produce the photoconductor shown in FIG. 4, a coating liquid for the protective layer 6 is prepared by dissolving the previously mentioned aromatic polycarbonate resin, optionally in combination with the binder agent, in a solvent, and the thus obtained coating liquid is coated on the charge transport layer 4 of the photoconductor shown in FIG. 3, and dried. It is preferable that the thickness of the protective layer 6 be in the range of 0.15 to 10 μm. It is preferable that the amount of aromatic polycarbonate resin for use in the protective layer 6 be in the range of 40 to 100 wt. % of the total weight of the protective layer 6.

The electrophotographic photoconductor shown in FIG. 5 can be produced by the following method:

The aromatic polycarbonate resin of the present invention, optionally in combination with the binder agent, is dissolved in a solvent to prepare a coating liquid for the charge transport layer 4. The thus prepared coating liquid is coated on the electroconductive support 1 and dried, whereby the charge transport layer 4 is provided on the electroconductive support 1. On the thus formed charge transport layer 4, a coating liquid prepared by dispersing the finely-divided particles of the charge generation material 3 in a solvent in which the binder agent may be dissolved when necessary, is coated, for example, by spray coating, and dried, so that the charge generation layer 5 is provided on the charge transport layer 4. The amount ratios of the components contained in the charge generation layer 5 and charge transport layer 4 are the same as those previously mentioned in the description of FIG. 3.

When the previously mentioned protective layer 6 is formed on the above prepared charge generation layer 5, the electrophotographic photoconductor shown in FIG. 6 can be fabricated.

To fabricate any of the aforementioned photoconductors of the present invention, a metallic plate or foil made of aluminum, a plastic film on which a metal such as aluminum is deposited, and a sheet of paper which has been treated so as to be electroconductive can be employed as the electroconductive support 1.

Specific examples of the binder agent used in the preparation of the photoconductor according to the present invention are condensation resins such as polyamide, polyurethane, polyester, epoxy resin, polyketone and polycarbonate; and vinyl polymers such as polyvinylketone, polystyrene, poly-N-vinylcarbazole and polyacrylamide. All the resins that have electrically insulating properties and adhesion properties can be employed. Some plasticizers may be added to the above-mentioned binder agents, when necessary. Examples of the plasticizer for use in the present invention are halogenated paraffin, dimethylnaphthalene and dibutyl phthalate. Further, a variety of additives such as an antioxidant, a light stabilizer, a thermal stabilizer and a lubricant may also be contained in the binder agents when necessary.

Furthermore, in the electrophotographic photoconductor according to the present invention, an intermediate layer such as an adhesive layer or a barrier layer may be interposed between the electroconductive support and the photoconductive layer when necessary. Examples of the material for use in the intermediate layer are polyamide, nitrocellulose, aluminum oxide and titanium oxide. It is preferable that the thickness of the intermediate layer be 1 μm or less.

When copying is performed by use of the photoconductor according to the present invention, the surface of the photoconductor is uniformly charged to a predetermined polarity in the dark. The uniformly charged photoconductor is exposed to a light image so that a latent electrostatic image is formed on the surface of the photoconductor. The thus formed latent electrostatic image is developed to a visible image by a developer, and the developed image is transferred to a sheet of paper. The electrophotographic photoconductor according to the present invention has excellent photosensitivity and durability.

Figure 7:
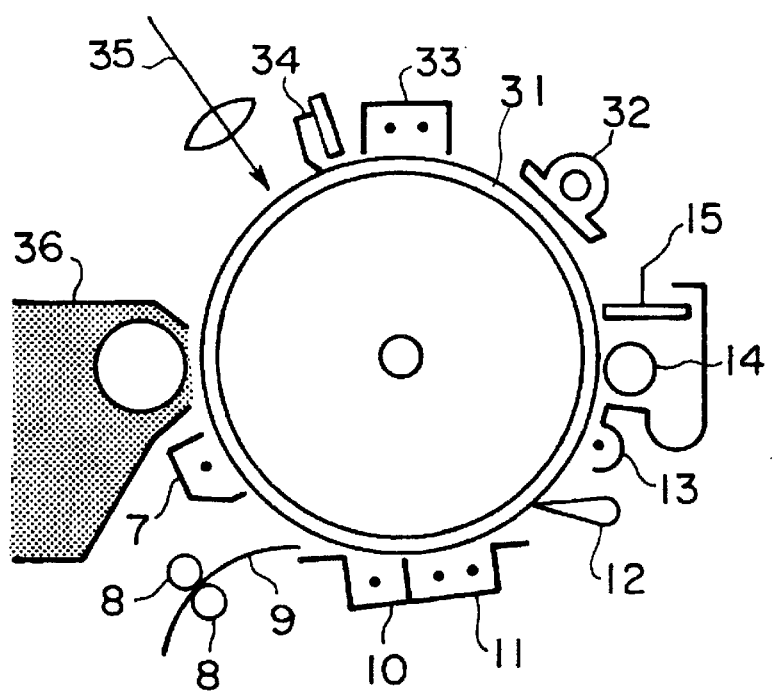
FIG. 7 is a schematic view showing an example of an electrophotographic image forming apparatus according to the present invention.

The electrophotographic process and apparatus will be next described with reference to FIGS. 7 through 9.

Referring to FIG. 1, designated as 31 is an electrophotographic photoconductor in the form of a drum having an electroconductive support, and a photoconductive layer formed thereon. The photoconductor 31 may be in the form of a sheet or an endless belt, if desired. Disposed to surround the photoconductor 31 are a charger 33, an eraser 34, a light exposing unit 35, a development unit 36, a pre-transfer charger 7, an image transfer charger 10, a separating charger 11, a separator 12, a pre-cleaning charger 13, a fur brush 14, a cleaning blade 15, and a quenching lamp 32. In FIG. 1, reference numeral 8 indicates resist rollers.

The charger 33, the pre-transfer charger 7, the image transfer charger 10, the separating charger 11, and the pre-cleaning charger 13 may be conventional means such as a corotron charger, a scorotron charger, a solid state charger, and a charging roller. Each of the chargers as mentioned above can be arranged in contact with the photoconductor 31 or may be disposed with a gap being defined therebetween. In each charger, it is possible to superimpose an alternate current component to a direct current component. It is effective to employ both the image transfer charger 10 and the separating charger 11 together as illustrated in FIG. 1.

As the light source of the light exposing unit 35 and the quenching lamp 32, there can be employed, for example, a fluorescent tube, tungsten lamp, halogen lamp, mercury vapor lamp, sodium lamp, light emitting diode (LED), semiconductor laser (LD) or electroluminescence (EL). Further, a desired wavelength can be obtained by use of various filters such as a sharp-cut filter, bandpass filter, near infrared cut filter, dichroic filter, interference filter and color conversion filter. The photoconductor may be irradiated with light in the course of the image transfer step, quenching step, cleaning step, or pre-light exposure step.

The toner image formed on the photoconductor 31 using the development unit 36 is transferred to a transfer sheet 9.

At the step of image transfer, all the toner particles deposited on the photoconductor 31 are not transferred to the transfer sheet 9. Some toner particles remain on the surface of the photoconductor 31. The remaining toner particles are removed from the photoconductor 31 using the fur brush 14 and the cleaning blade 15. The cleaning of the photoconductor may be carried out only by use of a cleaning brush. As the cleaning brush, there can be employed a conventional fur brush and magnetic fur brush.

When the photoconductor 31 is positively charged, and exposed to light images, positively-charged electrostatic latent images are formed on the photoconductor. In the similar manner as in above, when a negatively charged photoconductor is exposed to light images, negative electrostatic latent images are formed. A negatively-chargeable toner and a positively-chargeable toner are respectively used for development of the positive electrostatic images and the negative electrostatic images, thereby obtaining positive images. In contrast to this, when the positive electrostatic images and the negative electrostatic images are respectively developed using a positively-chargeable toner and a negatively-chargeable toner, negative images can be obtained on the surface of the photoconductor 31. Not only such development means, but also the quenching means may employ the conventional manner.

Figure 8:
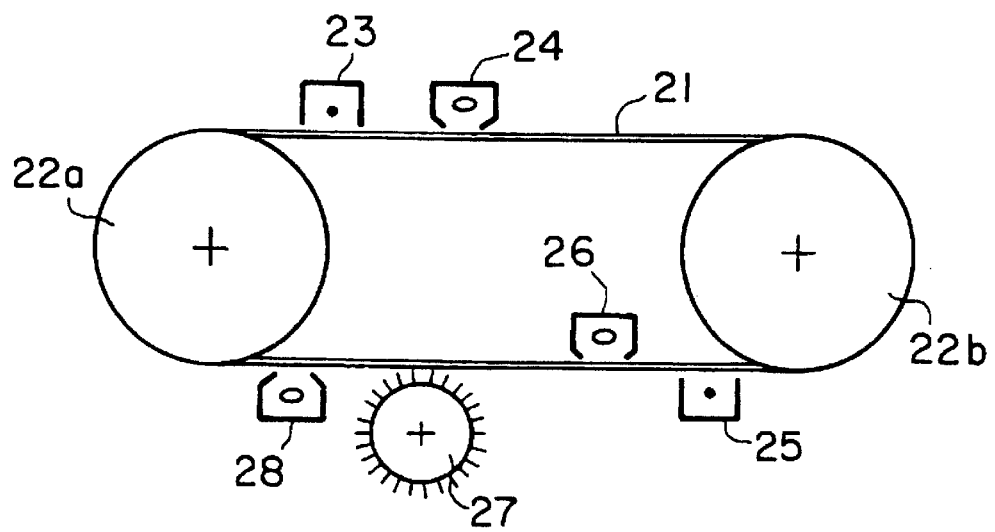
FIG. 8 is a schematic view showing another example of an electrophotographic image forming apparatus according to the present invention.

FIG. 8 is a schematic view which shows another example of the electrophotographic image forming apparatus according to the present invention. A photoconductor 21, which comprises an electroconductive support and the previously mentioned photoconductive layer formed thereon, is driven by driving rollers 22a and 22b. Charging of the photoconductor 21 is carried out by use of a charger 23, and the charged photoconductor 21 is exposed to light images using an image exposure light 24. Thereafter, latent electrostatic images formed on the photoconductor 21 are developed to toner images using a development unit (not shown), and the toner images are transferred to a transfer sheet with the aid of a transfer charger 25. After the toner images are transferred to the transfer sheet, the photoconductor 21 is subjected to pre-cleaning light exposure using a pre-cleaning light 26, and physically cleaned by use of a cleaning brush 27. Finally, quenching is carried out using a quenching lamp 28. In FIG. 8, the electroconductive support of the photoconductor 21 has light transmission properties, so that it is possible to apply the pre-cleaning light 26 to the electroconductive support side of the photoconductor 21.

The foregoing electrophotographic processes are merely illustrative of preferred embodiments of the present invention. Various modification and other embodiments may be used. For example, in the embodiment of FIG. 8, the photoconductive layer side of the photoconductor 21 may be exposed to the pre-cleaning light. Similarly, the image exposure light 24 and the quenching lamp 28 may be disposed so that light is directed toward the electroconductive support side of the photoconductor 21. While the photoconductor 21 is exposed to light using the image exposure light 24, pre-cleaning light 26, and the quenching lamp 28 in the embodiment of FIG. 2, light exposure for the photoconductor may be carried out by additionally providing any conventional exposing step such as exposure before image transfer or pre-exposure before the image exposure.

The above-discussed units, such as the charging unit, light-exposing unit, development unit, image transfer unit, cleaning unit, and quenching unit may be independently fixed in the copying machine, facsimile machine, or printer. Alternatively, at least one of those units may be incorporated in a process cartridge together with the photoconductor. To be more specific, the process cartridge is a single part or device which has the photoconductor and at least one of the charging unit, light-exposing unit, development unit, image transfer unit, cleaning unit and quenching unit and which is detachably set in the above-mentioned electrophotographic image forming apparatus.

Figure 9:
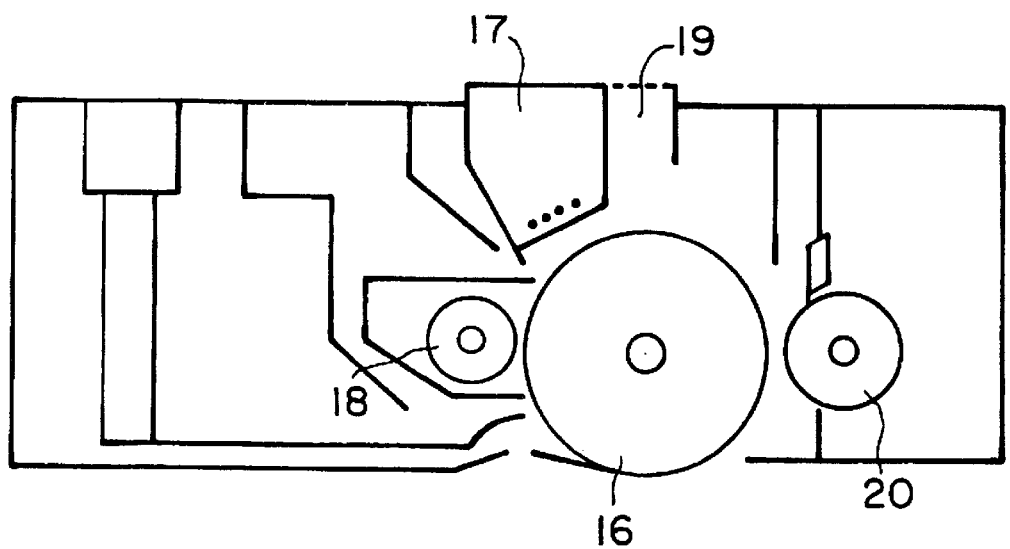
FIG. 9 is a schematic view showing an example of a process cartridge holding a photoconductor therein according to the present invention.

One example of the process cartridge according to the present invention is illustrated in FIG. 9. In this embodiment, designated as 16 is a photoconductor in the form of a drum comprising an electroconductive support and a charge generation layer. Disposed around the photoconductor 16 are a charger 17, a light exposing unit 19, a development roller 20 and a cleaning brush 18. The photoconductor 16 may be in the form of a sheet or an endless belt, if desired.

The following examples will further illustrate the present invention. Parts are by weight.

EXAMPLE 1

6.15 Grams of 3-methyl-4'-[2-(4-methoxyphenethyl)]-diphenylamine, 4.54 g of 4,4'-diiodo-3,3-dimethylbiphenyl, 7.22 g of potassium carbonate anhydride, 0.20 g of copper powder and 40 ml of o-dichlorobenzene were charged in a flask and the mixture was heated in nitrogen flow for 40 hours under reflux. The reaction mixture was cooled to room temperature and filtered to remove insoluble matters. The filtrate was then distilled to remove the solvent under a reduced pressure, thereby obtaining a light brown oily liquid. The oily liquid was subjected to silica gel column chromatography (eluent; toluene) and the isolated product was recrystallized from a mixed solvent of ethyl acetate/ethanol to obtain 5.13 g of N,N'-di-m-tolyl-N,N'-bis-4-[2-(4-methoxyphenethyl)phenyl]-3,3'-dimethylbenzidine in the form of colorless needle crystals having a melting point of 145.0–146.0° C. Elemental analysis (%); measured value (calculated value): C: 85.32 (85.66), H: 7.00 (6.69), N: 2.98 (3.45)

EXAMPLE 2

Figure 10:
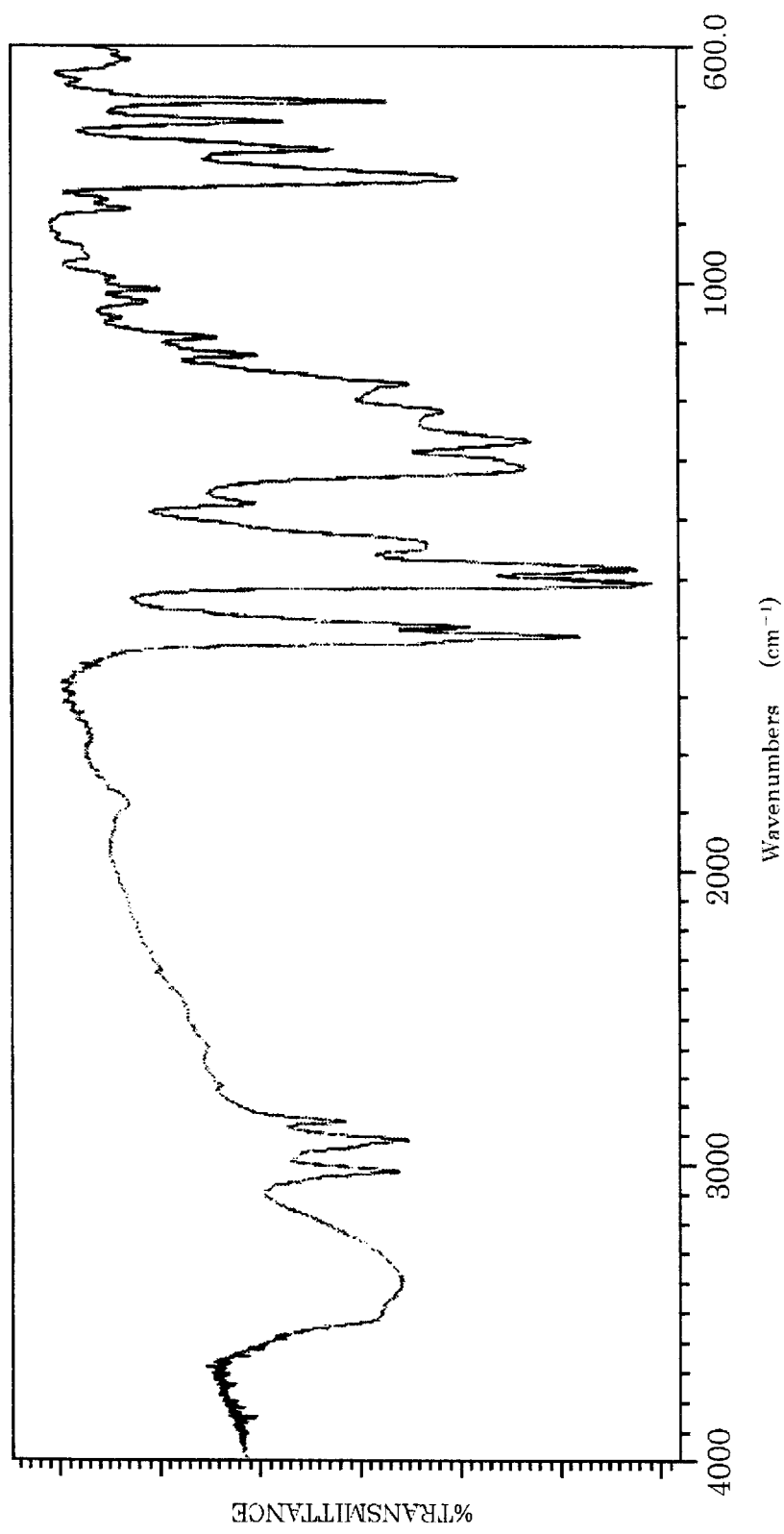
FIGS. 10 to 19 are IR spectra of aromatic polycarbonate resins obtained in Examples 2, 4, 6 and 8 through 14, respectively.

4.53 Grams of the dimethoxy compound obtained in Example 1 were dissolved in 40 ml of dried methylene chloride, to which a solution of 2.79 g of boron tribromide dissolved in 7 ml of methylene chloride was added dropwise at −5 to −1° C. in nitrogen flow through 35 minutes. This was then stirred at room temperature for one hour to complete the reaction. The reaction mixture was mixed with water and extracted with ethyl acetate. The organic layer was washed with 5% aqueous solution of sodium hydrogen carbonate and then with water. The solvent was removed by distillation under a reduced pressure to leave a light brown oil. The oil was subjected to silica gel column chromatography (eluent; toluene/ethyl acetate=10/1 vol.) to obtain 3.17 g of N,N'-di-m-tolyl-N,N'-bis-4-[2-(4-hydroxyphenethyl)phenyl]-3,3-dimethylbenzidine in the form of a colorless glass, whose infrared absorption spectrum (KBr tablet) was as shown in FIG. 10. Elemental analysis (%); measurement value (calculated value): C: 85.47 (85.66), H: 6.83 (6.69), N: 3.21 (3.57)

EXAMPLE 3

9.97 Grams of N,N'-bis(3-methyl-4-formylphenyl)-4-methylbiphenyl-4'-amine and 12.66 g of 4-diethyl methoxybenzylphosphonate were dissolved in 75 ml of dried N-N'-dimethylformamide, to which 6.95 g of potassium-tert-butoxide were gradually added at room temperature. After having been stirred at room temperature for one hour, this was neutralized with acetic acid and pored into ice water. The precipitates were filtered and washed with water, and then dried to obtain 13.75 g of a distyryl compound in the form of yellow powder. This was dissolved in 70 ml of tetrahydrofuran and hydrogenated using 1.4 g of 5% Pd-carbon. After the hydrogenation, the catalyst was removed with a filter aid, and the solvent was removed by distillation under a reduced pressure, thereby obtaining 11.50 g of N,N'-bis{3-methyl-4[2-(4-methoxy)-phenethyl]}phenyl-4-methylbiphenyl-4'-amine in the form of a colorless oil.

EXAMPLE 4

Figure 11:
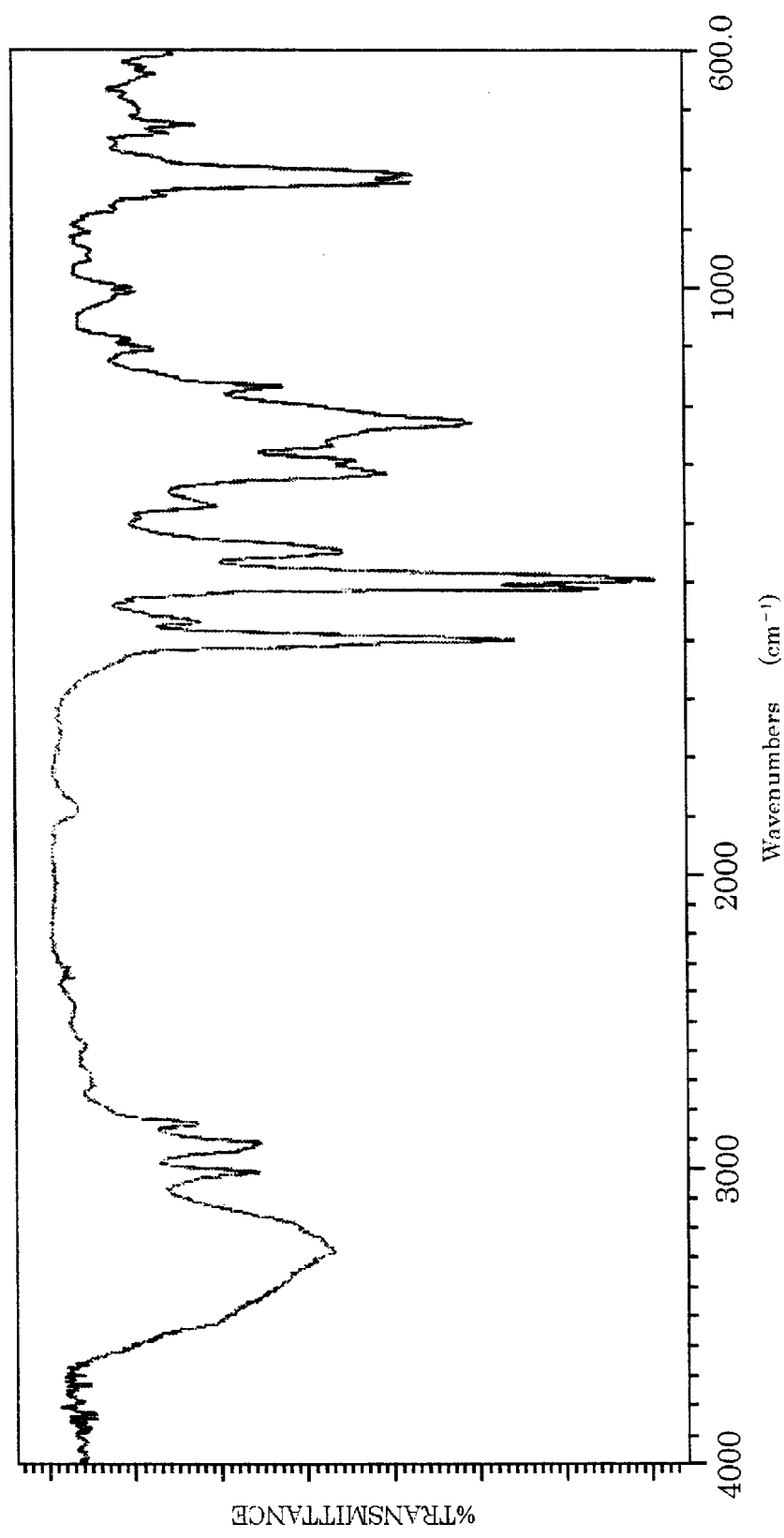

The dimethoxy compound obtained in Example 3 was dissolved in 80 ml of dried methylene chloride, to which a solution of 8.97 g of boron tribromide dissolved in 22 ml of methylene chloride was added dropwise at −7 to −2° C. in nitrogen flow through 40 minutes. This was then stirred at room temperature for one hour to complete the reaction. The reaction mixture was mixed with water and extracted with ethyl acetate. The organic layer was washed with 5% aqueous solution of sodium hydrogen carbonate and then with water. The solvent was removed by distillation under a reduced pressure to leave a light brown oil. The oil was subjected to silica gel column chromatography (eluent; toluene/ethyl acetate=4/1 vol.) to obtain 8.12 g of N,N'-bis{3-methyl-4[2-(4-hydroxy)phenethyl]}phenyl-4-methylbiphenyl-4'-amine in the form of colorless fine powder, whose TG-DTA endothermic peak was present at 108.4° C. and whose infrared absorption spectrum (KBr tablet) was as shown in FIG. 11. Elemental analysis (%); measurement value (calculated value): C: 85.66 (85.52), H:6.89 (6.86), N: 2.18 (2.32)

EXAMPLE 5

6.0 Grams of 4,4'-bis[2-(4-methoxyphenethyl)]-diphenylamine, 7.04 g of 2-iodine-9,9-dimethylfluorene, 11.4 g of potassium carbonate anhydride, 0.20 g of copper powder and 50 ml of nitrobenzene were charged in a flask and the mixture was heated in nitrogen flow for 3.5 hours under reflux. The reaction mixture was cooled to room temperature and filtered to remove insoluble matters. The filtrate was then distilled to remove the solvent under a reduced pressure, thereby obtaining a light brown oily liquid. The oily liquid was subjected to silica gel column chromatography (eluent; toluene) to obtain 6.55 g of N,N'-bis{4-[2-(4-methoxy)phenethyl]}phenyl-9,9-dimethylfluorene-2-amine in the form of yellow oil.

EXAMPLE 6

Figure 12:
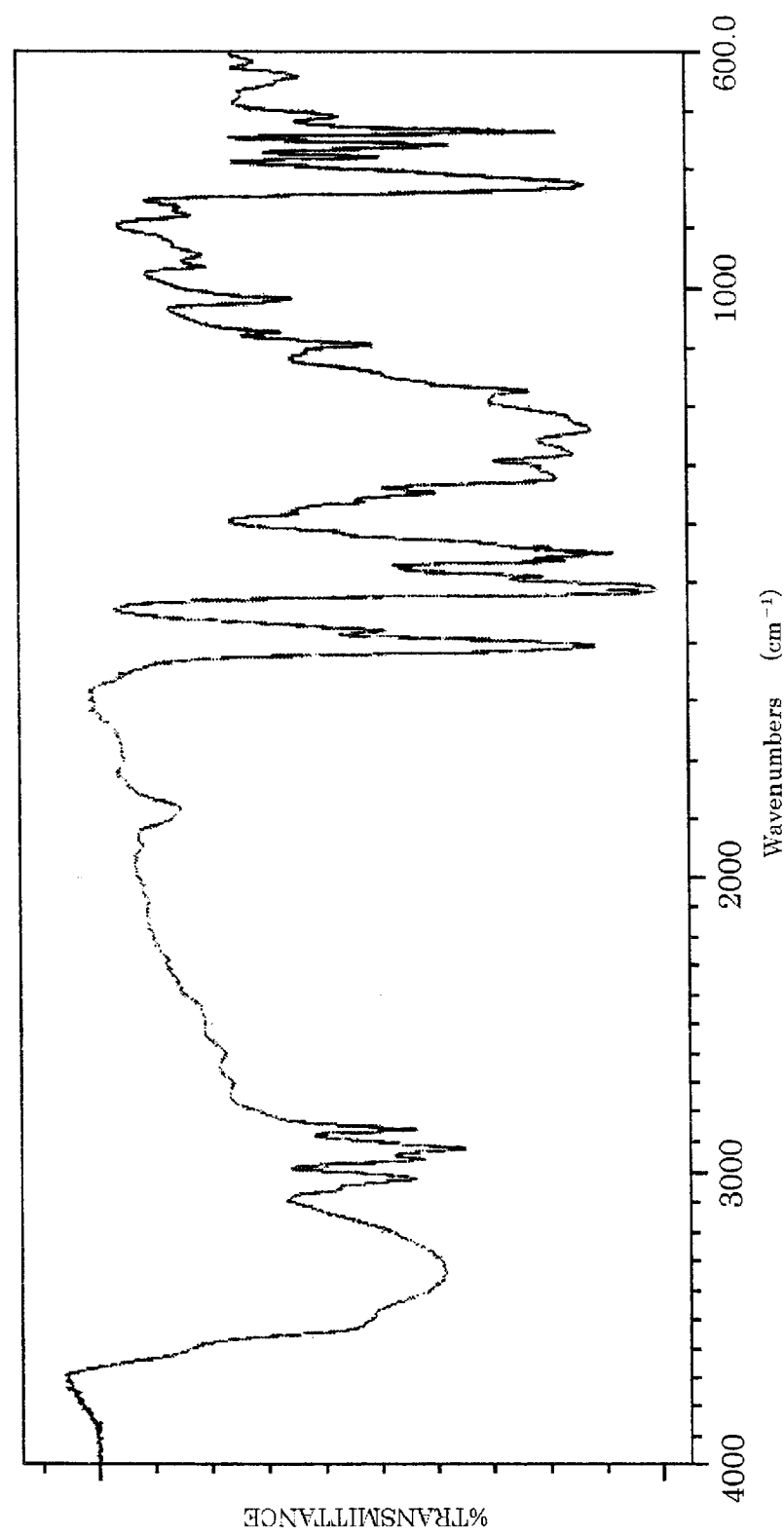

The dimethoxy compound obtained in Example 5 was dissolved in 40 ml of dried methylene chloride, to which a solution of 5.18 g of boron tribromide dissolved in 10 ml of methylene chloride was added dropwise at −3 to −1° C. in nitrogen flow through 20 minutes. This was then stirred at room temperature for two hours to complete the reaction. The reaction mixture was mixed with water and extracted with ethyl acetate. The organic layer was washed with 5% aqueous solution of sodium hydrogen carbonate and then with water. The solvent was removed by distillation under a reduced pressure to leave a light brown oil. The oil was subjected to silica gel column chromatography (eluent; dichloroethane), thereby obtaining 3.92 g of N,N'-bis{4-[2-(4-hydroxy)phenethyl]}phenyl-9,9-dimethylfluorene-2-amine in the form of light yellow glass, whose TG-DTA endothermic peak was not observed and whose infrared absorption spectrum (KBr tablet) was as shown in FIG. 12.

Elemental analysis (%); measurement value (calculated value): C: 85.45 (85.81), H: 6.46 (6.55), N: 2.06 (2.33)

EXAMPLE 7

4.23 Grams of N,N'-diphenyl-N,N'-bis(4-formylphenyl)diphenyl ether-4,4'-diamine and 4.10 g of 4-diethyl methoxybenzylphosphonate were dissolved in 50 ml of dried N,N'-dimethylformamide, to which 2.65 g of potassium-tert-butoxide was gradually added at room temperature. After having been stirred at room temperature for two hours, this was neutralized with acetic acid and pored into ice water. The precipitates were filtered and washed with water, and then dried to obtain 5.52 g of distyryl compound in the form of colorless powder. The distyryl compound was dissolved in 200 ml of tetrahydrofuran and hydrogenated using 0.6 g of 5% Pd-carbon. After the hydrogenation, the catalyst was removed with a filter aid, and the solvent was removed by distillation under a reduced pressure, thereby obtaining 4.95 g of N,N'-diphenyl-N,N'-bis{4-[2-(4-methoxyphenethyl)phenyl]}diphenyl ether-4,4'-diamine in the form of colorless crystals, whose TG-DTA endothermic peak temperature was 134.1° C.

EXAMPLE 8

Figure 13:
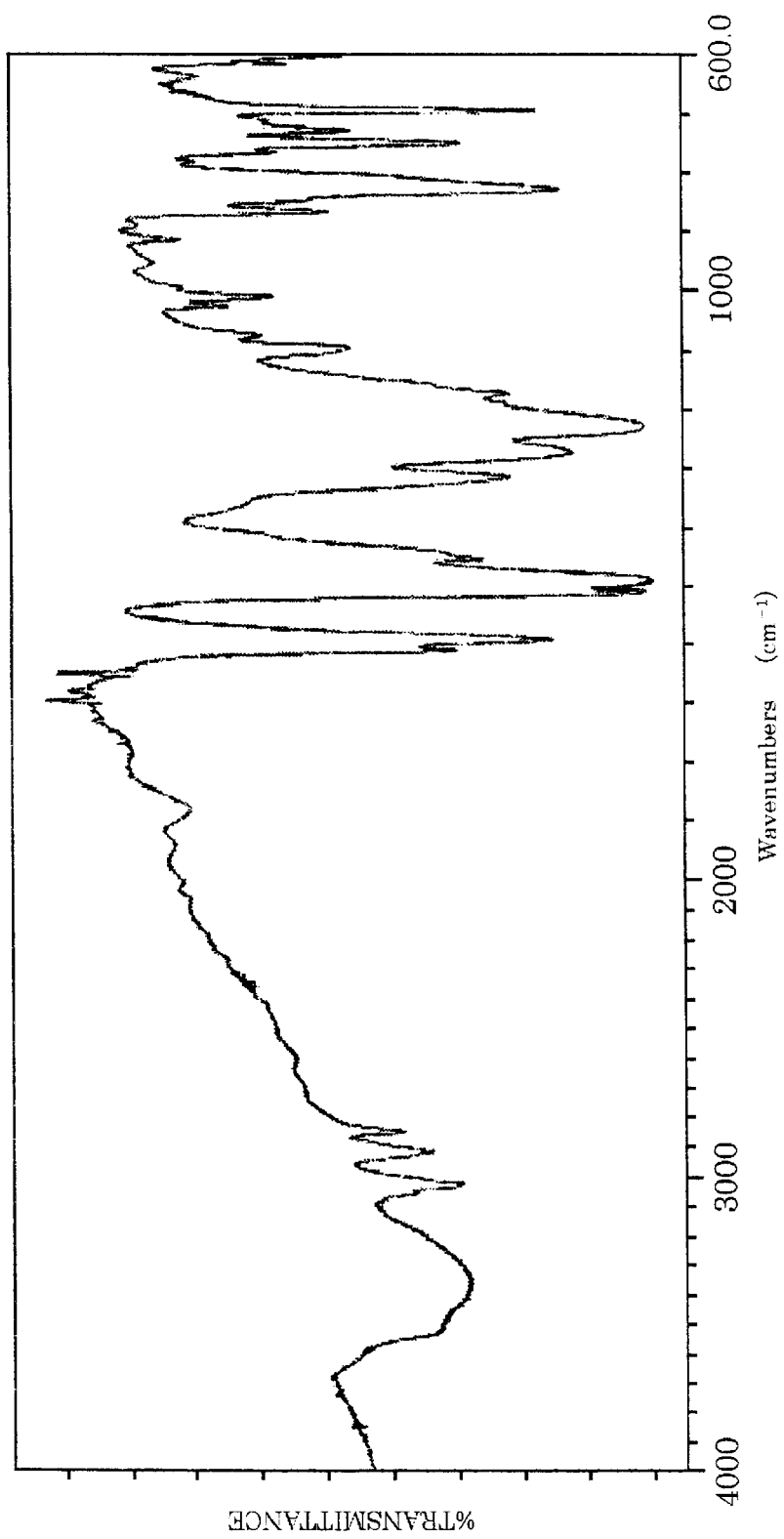

4.40 Grams of dimethoxy compound obtained in Example 7 were dissolved in 50 ml of dried methylene chloride, to which a solution of 2.85 g of boron tribromide dissolved in 8 ml of methylene chloride was added dropwise at −4 to −3° C. in nitrogen flow through 20 minutes. This was then stirred at room temperature for two hours to complete the reaction. The reaction mixture was mixed with water and extracted with ethyl acetate. The organic layer was washed with 5% aqueous solution of sodium hydrogen carbonate and then with water. The solvent was removed by distillation under a reduced pressure to leave a light brown oil. The oil was subjected to silica gel column chromatography (eluent; toluene/ethyl acetate=4/1 vol/vol), thereby obtaining 4.10 g of N,N'-diphenyl-N,N'-bis-4-[2-(4-hydroxyphenethyl)phenyl]diphenyl ether-4,4'-diamine in the form of colorless glass, whose TG-DTA endothermic peak was not observed and whose infrared absorption spectrum (KBr tablet) was as shown in FIG. 13.

Elemental analysis (%) measurement value (calculated value) C: 83.52 (83.83), H: 5.80 (5.97), N: 3.55 (3.76)

EXAMPLE 9

A mixture containing 2.30 g of the diphenol compound obtained in Example 2, 5.7 mg of 4-tert-butylphenol and a solution of 0.87 g of sodium hydroxide and 27 mg of sodium hydrosulfite dissolved in 15 ml of water was stirred at room temperature in nitrogen flow for 30 minutes. To this mixture a solution of 0.40 g of bis(trichloromethyl)-carbonate dissolved in 9 ml of methylene chloride was poured at a time at 20° C. with vigorous stirring. After stirring for 15 minutes, a drop of trimethylamine was added to the reaction mixture and the reaction was further continued at room temperature for one hour with stirring. The resulting mixture was then diluted with methylene chloride and the organic layer was separated and washed with ion exchange water twice and then with 2% aqueous solution of hydrochloric acid. The washing was repeated until the electric conductivity of the aqueous layer became approximately the same as that of ion exchange water. The organic layer was then added dropwise to a large quantity of methanol. The precipitates were filtered and dried, thereby obtaining 1.77 g of a colorless polycarbonate resin represented by the following formula.

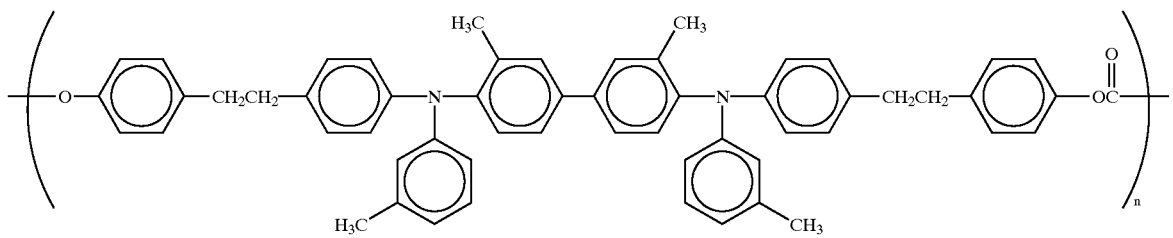

Figure 14:
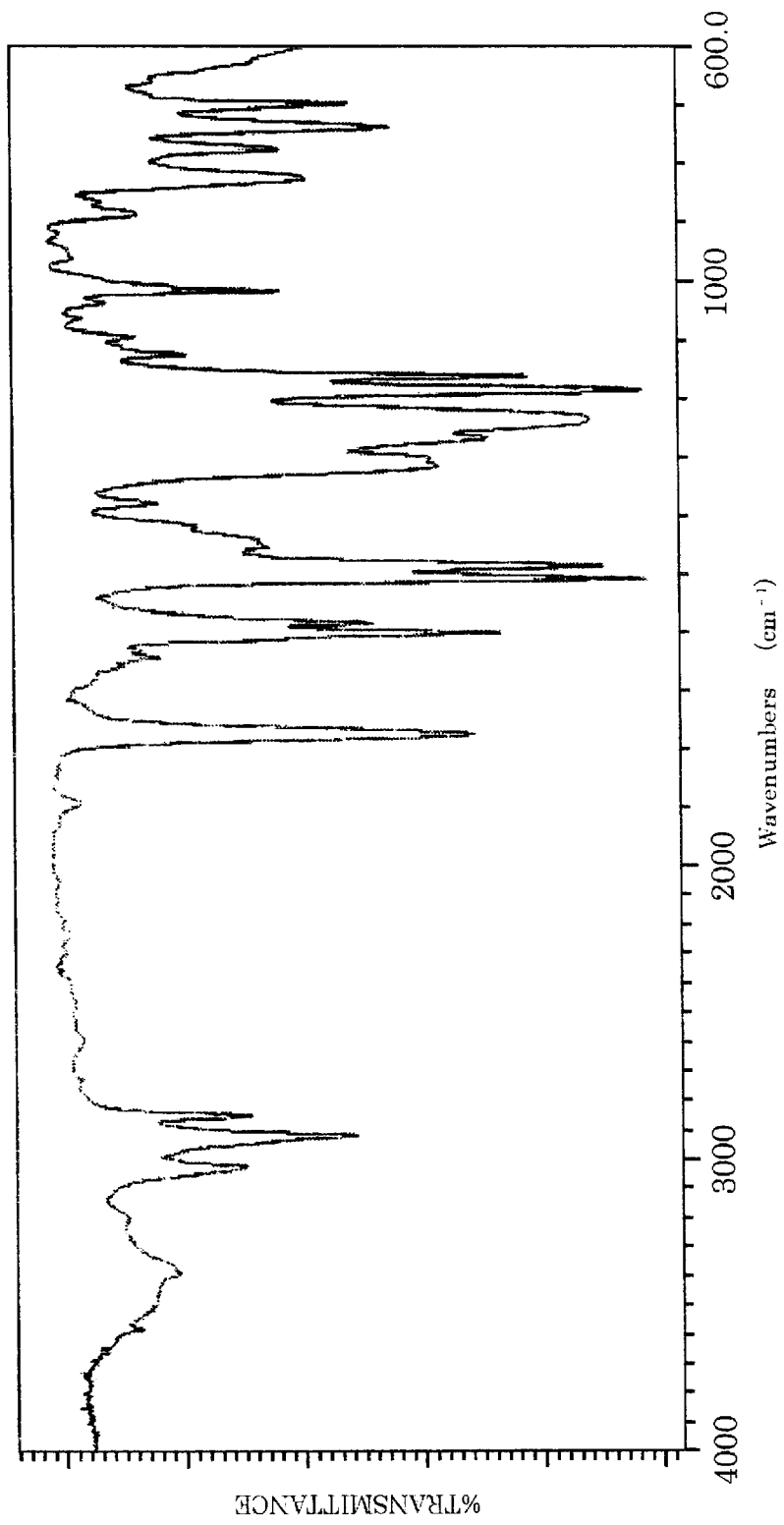

The polystyrene-reduced weight average molecular weight (Mn) and the number average molecular weight (Mw) of the polycarbonate resin, which were measured by gel permeation chromatography, were 45800 and 205800, respectively. The glass transition point (Tg) of the polycarbonate resin, which was obtained by differential scanning calorimetry, was 143.7° C. The infrared absorption spectrum of the polycarbonate resin (thin film) was as shown in FIG. 14. Elemental analysis (%); measurement value (calculated value): C: 84.29 (84.40), H: 6.16 (6.23), N: 3.23 (3.45)

EXAMPLE 10

A mixture containing 3.02 g of the diphenol compound obtained in Example 4, 9.8 mg of 4-tert-butylphenol and a solution of 1.50 g of sodium hydroxide and 46 mg of sodium hydrosulfite dissolved in 20 ml of water was stirred at room temperature in nitrogen flow for 30 minutes. To this mixture, a solution of 0.74 g of bis(trichloromethyl)-carbonate added at a time at 20° C. with vigorous stirring. After stirring for 15 minutes, a drop of trimethylamine was added to the reaction mixture, and the reaction was further continued at room temperature for one hour with stirring. The resulting mixture was then diluted with methylene chloride and the organic layer was separated and washed with ion exchange water twice and then with 2% aqueous solution of hydrochloric acid. The washing was repeated until the electric conductivity of the aqueous layer became approximately the same as that of ion exchange water. The organic layer was then added dropwise to a large quantity of methanol. The precipitates were filtered and dried, thereby obtaining 2.76 g of a colorless polycarbonate resin represented by the following formula.

Figure 15:
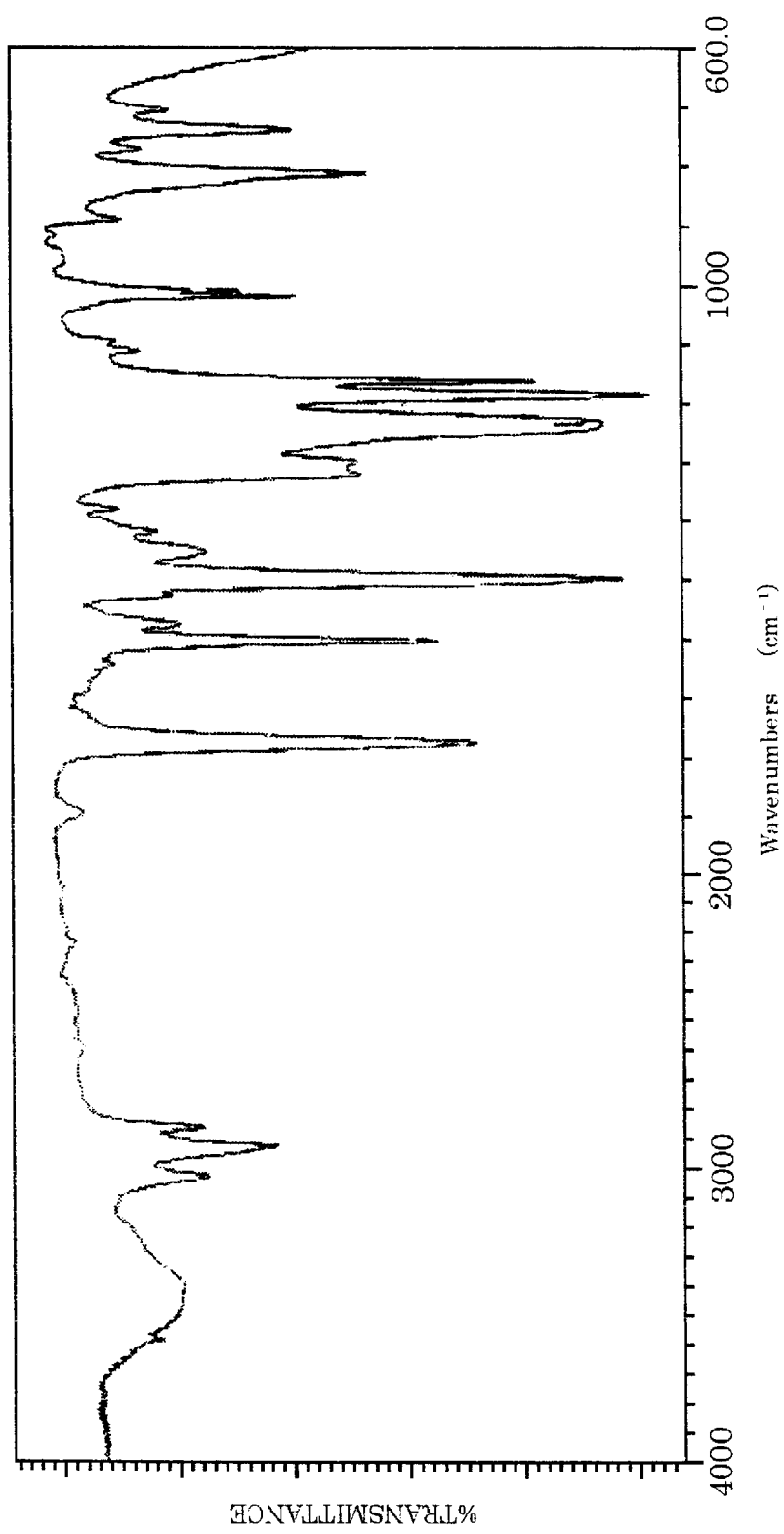

The polystyrene-reduced weight average molecular weight (Mn) and the number average molecular weight (Mw) of the polycarbonate resin, which were measured by gel permeation chromatography, were 67100 and 229000, respectively. The glass transition point (Tg) of the polycarbonate resin, which was obtained by differential scanning calorimetry, was 140.4° C. The infrared absorption spectrum of the polycarbonate resin (thin film) was as shown in FIG. 15.

Elemental analysis (%); measurement value (calculated value): C: 83.81 (83.90), H: 6.20 (6.25), N: 2.08 (2.22)

EXAMPLE 11

A mixture containing 3.28 g of the diphenol compound obtained in Example 6, 14.0 mg of 4-tert-butylphenol and a solution of 1.65 g of sodium hydroxide and 51 mg of sodium hydrosulfite dissolved in 22 ml of water was stirred at room temperature in nitrogen flow for 30 minutes. To this mixture a solution of 0.81 g of bis(trichloromethyl)-carbonate dissolved in 17 ml of methylene chloride was added at a time at 20° C. with vigorous stirring. After stirring for 15 minutes, a drop of trimethylamine was added to the reaction mixture and the reaction was further continued at room temperature for one hour with stirring. The reaction mixture was diluted with methylene chloride and the organic layer was separated and washed with ion exchange water twice and then with 2% aqueous solution of hydrochloric acid. The washing was repeated until the electric conductivity of the aqueous layer became approximately the same as that of ion exchange water. The organic layer was then added dropwise to a large quantity of methanol. The precipitates were filtered and dried, thereby obtaining 2.85 g of a light yellow polycarbonate resin represented by the following formula.

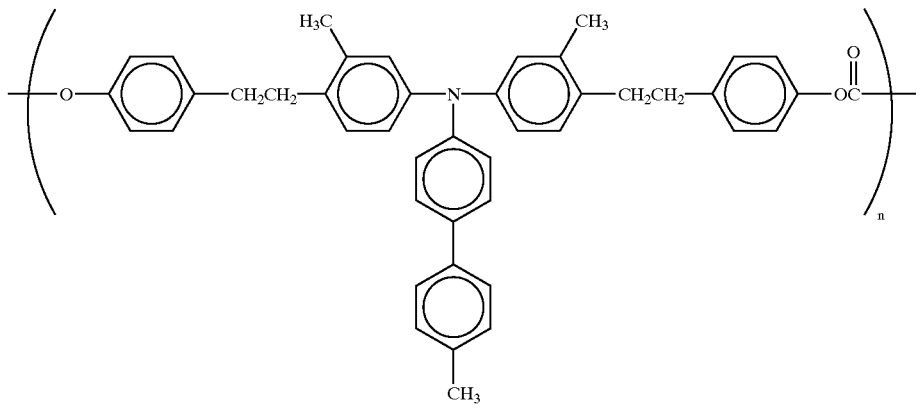

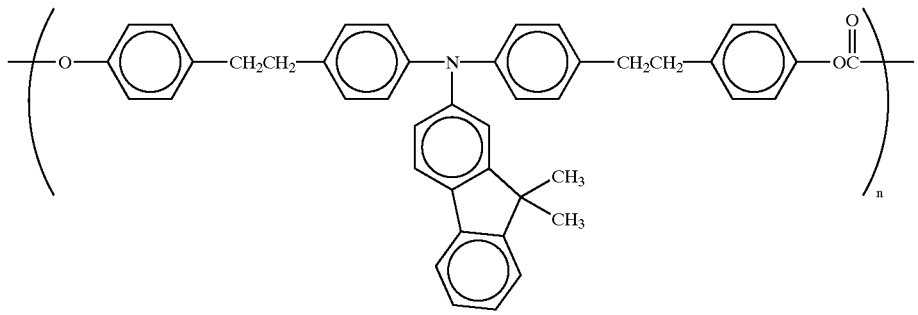

Figure 16:
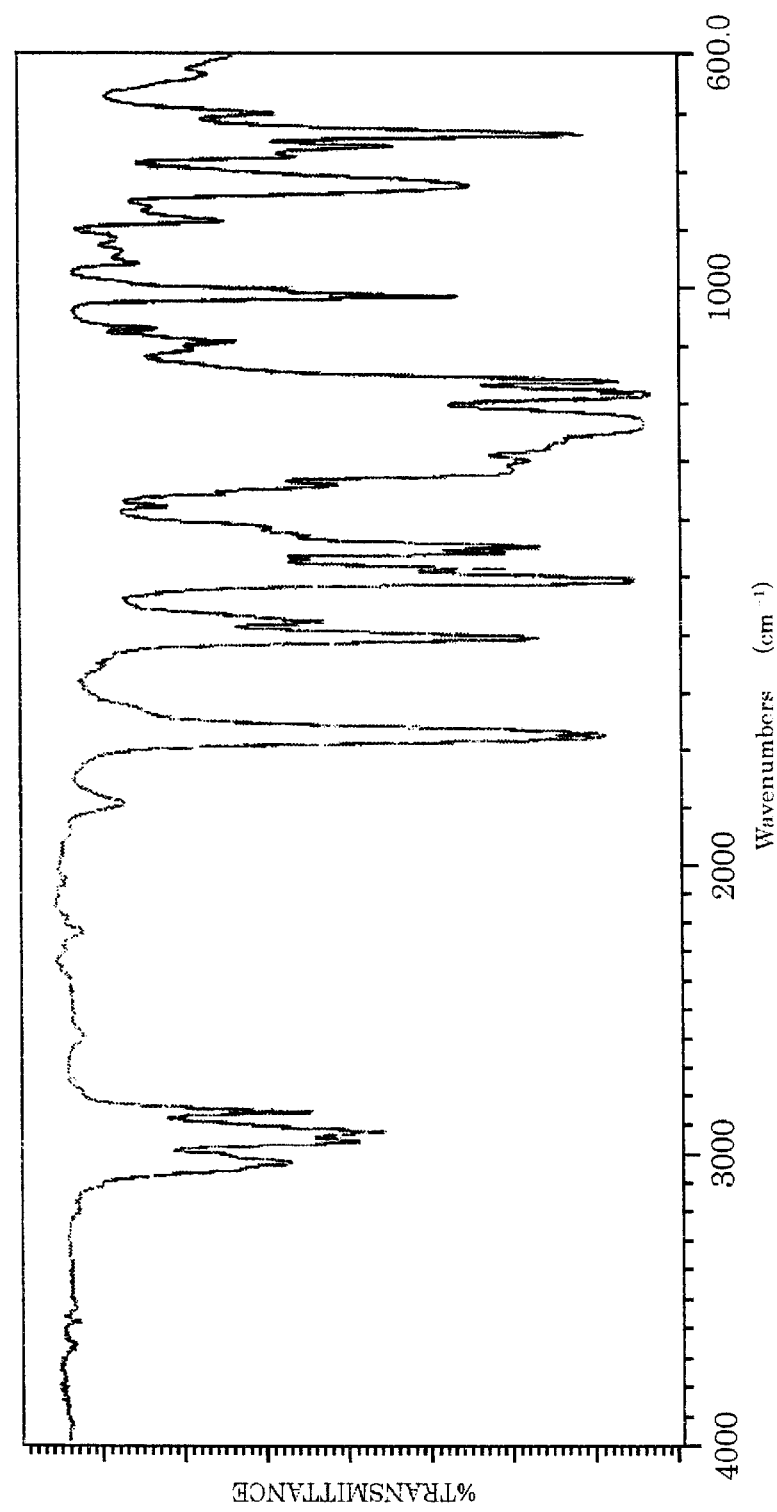

The polystyrene-reduced weight average molecular weight (Mn) and the number average molecular weight (Mw) of the polycarbonate resin, which were measured by gel permeation chromatography, were 52800 and 173900, respectively. The glass transition point (Tg) of the polycarbonate resin, which was obtained by differential scanning calorimetry, was 151.2° C. The infrared absorption spectrum of the polycarbonate resin (thin film) was as shown in FIG. 16. Elemental analysis (%) measurement value (calculated value): C: 83.91 (84.17), H: 5.85 (5.95), N: 2.00 (2.23)

EXAMPLE 12

A mixture containing 4.33 g of the diphenol compound obtained in Example 2, 1.39 g of 1,1-bis(4-hydroxylphenyl) cyclohexane, 26 mg of 4-tert-butylphenol and a solution of 3.21 g of sodium hydroxide and 100 mg of sodium hydrosulfite dissolved in 40 ml of water was stirred at room temperature in nitrogen flow for 30 minutes. To this mixture a solution of 1.48 g of bis(trichloromethyl)carbonate dissolved in 33 ml of methylene chloride was added at a time at 20° C. with vigorous stirring. After stirring for 30 minutes, a drop of trimethylamine was added to the reaction mixture and the reaction was further continued at room temperature for one hour with stirring. The resulting mixture was diluted with methylene chloride and the organic layer was separated and washed with ion exchange water twice and then with 2% aqueous solution of hydrochloric acid. The washing was repeated until the electric conductivity of the aqueous layer became approximately the same as that of ion exchange water. The organic layer was then added dropwise to a large quantity of methanol. The precipitates were filtered and dried, thereby obtaining 5.12 g of a colorless polycarbonate resin represented by the following formula.

Figure 17:
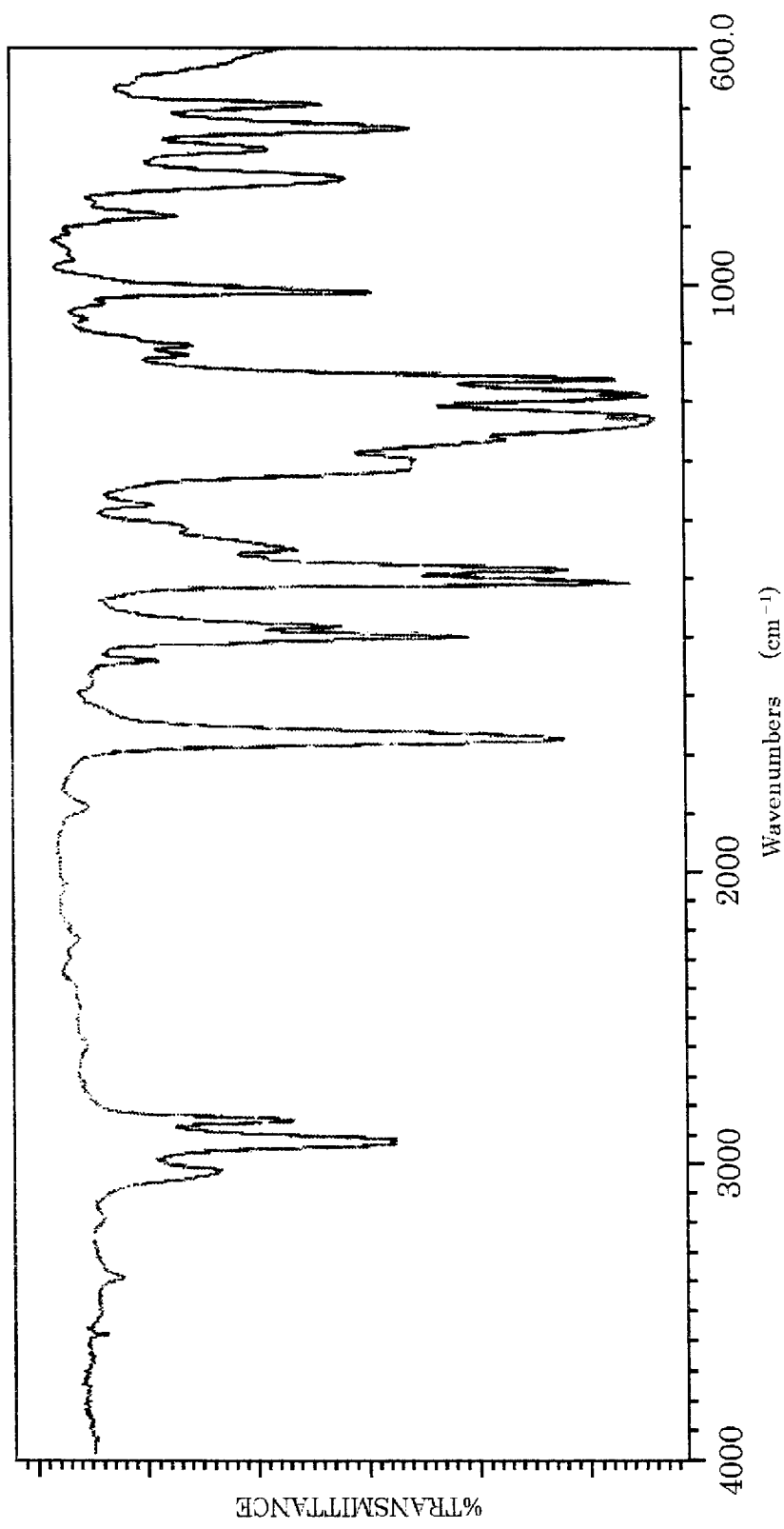

The polystyrene-reduced weight average molecular weight (Mn) and the number average molecular weight (Mw) of the polycarbonate resin, which were measured by gel permeation chromatography, were 50200 and 143100, respectively. The glass transition point (Tg) of the polycarbonate resin, which was obtained by differential scanning calorimetry, was 152.3° C. The infrared absorption spectrum of the polycarbonate resin (thin film) was as shown in FIG. 17.

Elemental analysis (%); measurement value (calculated value): C: 82.46 (82.66), H: 6.15 (6.20), N: 2.30 (2.57)

EXAMPLE 13

A mixture containing 4.86 g of the diphenol compound obtained in Example 4, 0.67 g of 1,1-bis(4-hydroxylphenyl) cyclohexane, 25 mg of 4-tert-butylphenol and a solution of 3.16 g of sodium hydroxide and 96 mg of sodium hydrosulfite dissolved in 40 ml of water was stirred at room temperature in nitrogen flow for 30 minutes. To this mixture a solution of 1.46 g of bis(trichloromethyl)carbonate dissolved in 35 ml of methylene chloride was added at a time at 20° C. with vigorous stirring. After stirring for 15 minutes, a drop of trimethylamine was added to the reaction mixture and the reaction was further continued at room temperature for one hour with stirring. The resulting mixture was diluted with methylene chloride and the organic layer was separated and washed with ion exchange water twice and then with 2% aqueous solution of hydrochloric acid. The washing was repeated until the electric conductivity of the aqueous layer became approximately the same as that of ion exchange water. The organic layer was then added dropwise to a large quantity of methanol. The precipitates were filtered and dried, thereby obtaining 5.18 g of a colorless polycarbonate resin represented by the following formula.

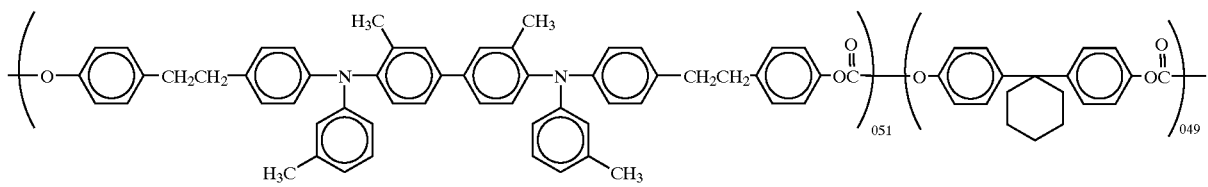

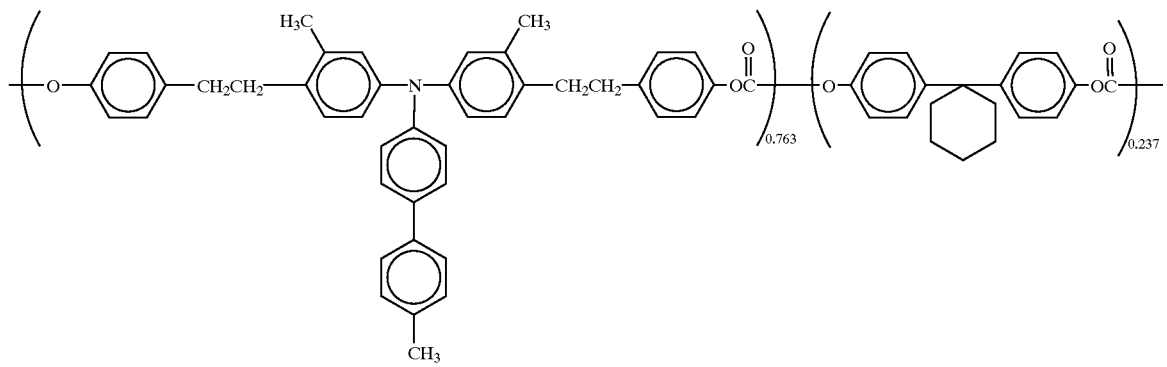

Figure 18:
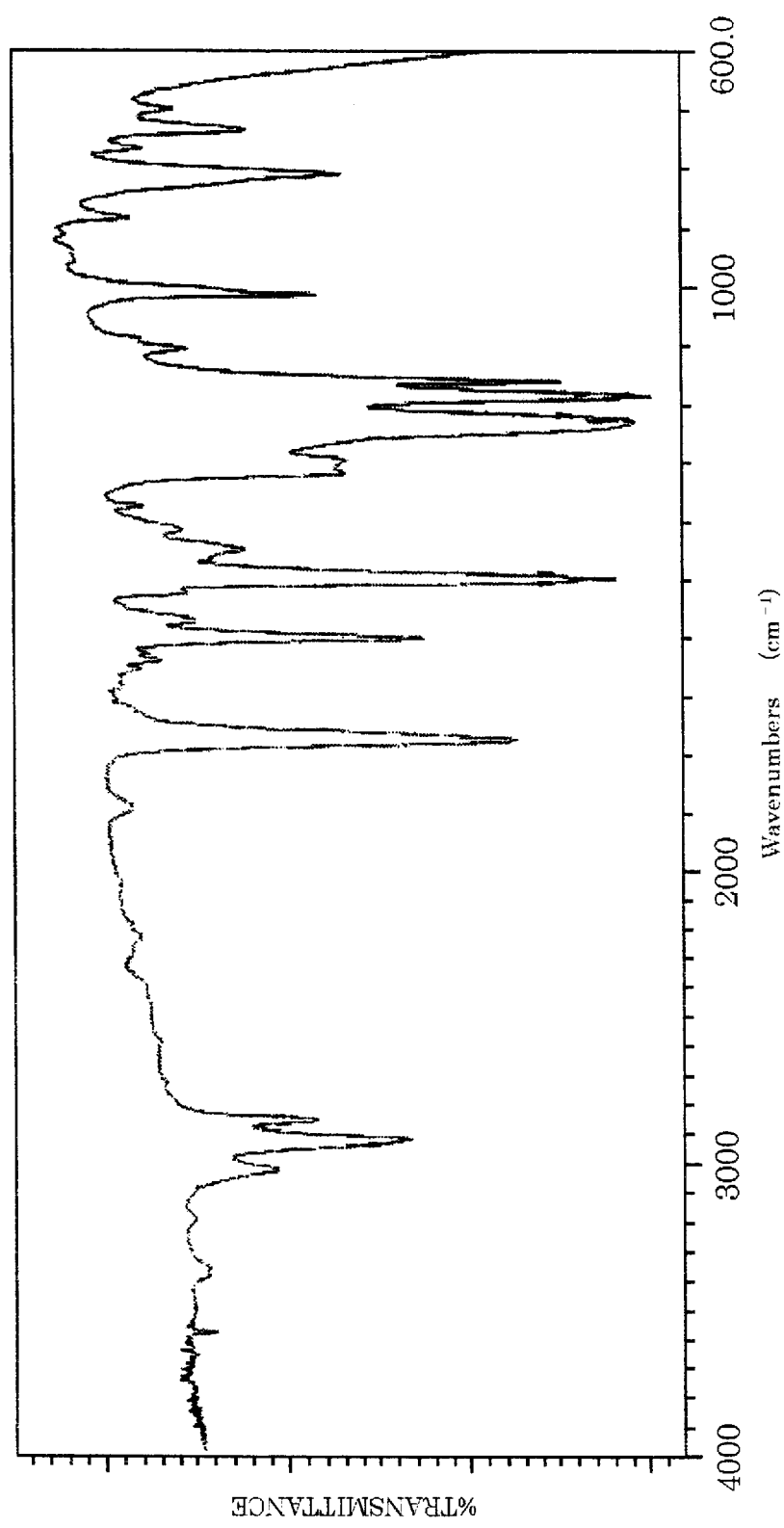

The polystyrene-reduced weight average molecular weight (Mn) and the number average molecular weight (Mw) of the polycarbonate resin, which were measured by gel permeation chromatography, were 53700 and 188800, respectively. The glass transition point (Tg) of the polycarbonate resin, which was obtained by differential scanning calorimetry, was 145.3° C. The infrared absorption spectrum of the polycarbonate resin (thin film) was as shown in FIG. 18. Elemental analysis (%); measurement value (calculated value): C: 82.92 (83.10), H: 6.18 (6.23), N: 1.75 (1.94)

EXAMPLE 14

A mixture containing 3.70 g of the diphenol compound obtained in Example 8, 1.06 g of 1,1-bis(4-hydroxylphenyl)cyclohexane, 16 mg of 4-tert-butylphenol and a solution of 2.68 g of sodium hydroxide and 83 mg of sodium hydrosulfite dissolved in 33 ml of water was stirred at room temperature in nitrogen flow for 30 minutes. To this mixture, a solution of 1.59 g of bis(trichloromethyl)carbonate dissolved in 33 ml of methylene chloride was added thereto at a time at 20° C. with vigorous stirring. After stirring for 15 minutes, a drop of trimethylamine was added to the reaction mixture and the reaction was further continued at room temperature for one hour with stirring. The resulting reaction mixture was diluted with methylene chloride and the organic layer was separated and washed with ion exchange water twice and then with 2% aqueous solution of hydrochloric acid. The washing was repeated until the electric conductivity of the aqueous layer became approximately the same as that of ion exchange water. The organic layer was then added dropwise to a large quantity of methanol. The precipitates were filtered and dried, thereby obtaining 4.40 g of a colorless polycarbonate resin represented by the following formula.

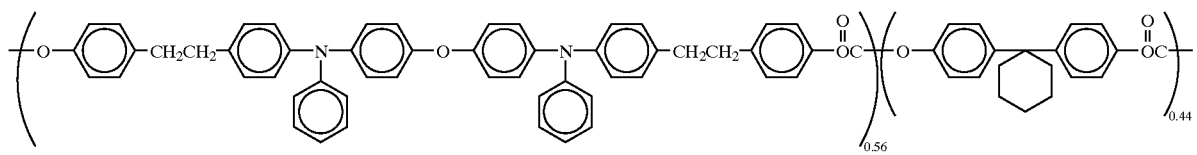

Figure 19:
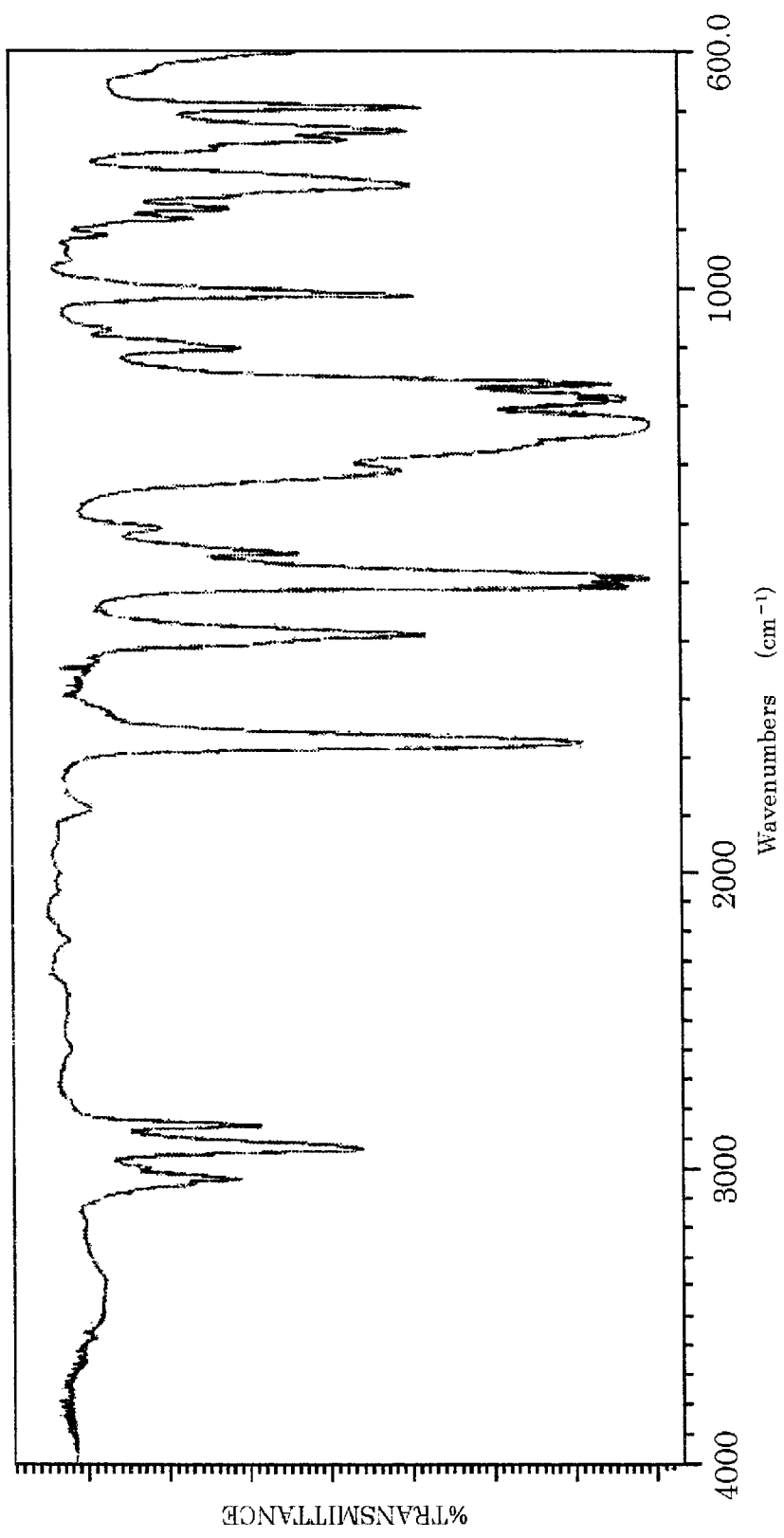

The polystyrene-reduced weight average molecular weight (Mn) and the number average molecular weight (Mw) of the polycarbonate resin, which were measured by gel permeation chromatography were 67300 and 190000, respectively. The glass transition point (Tg) of the polycarbonate resin, which was obtained by differential scanning calorimetry, was 143.9° C. The infrared absorption spectrum of the polycarbonate resin (thin film) was as shown in FIG. 19. Elemental analysis (%); measurement value (calculated value): C: 81.60 (81.40), H: 5.60 (5.65), N: 2.62 (2.79)

EXAMPLE 15–23

Polycarbonate resins represented by the following formulas were prepared in a manner similar to that described in Example 14. The glass transition points (Tg), the elemental analysis values, and the polystyrene-reduced number average molecular weight (Mn) and weight average molecular weight (Mw) measured by gel permeation chromatography of these polycarbonate resins are summarized in Table 1.

Polycarbonate of Example 15
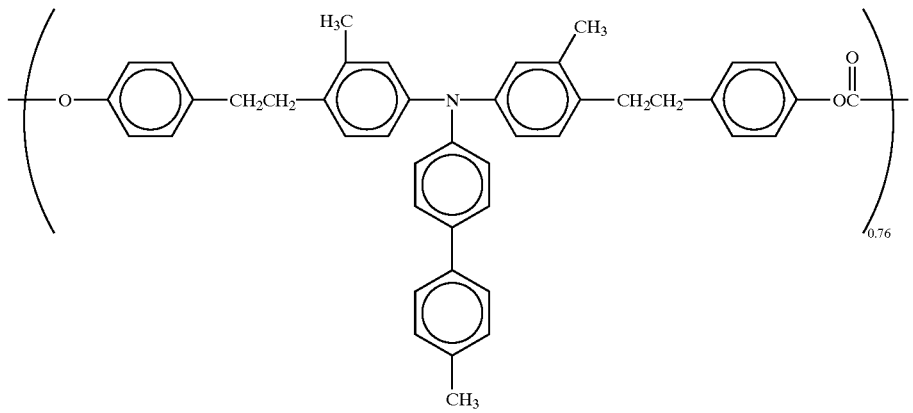
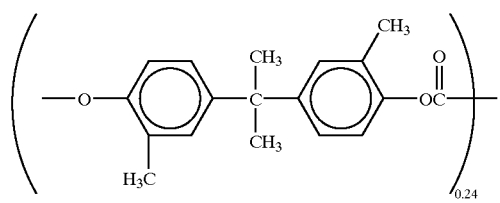
Polycarbonate of Example 16
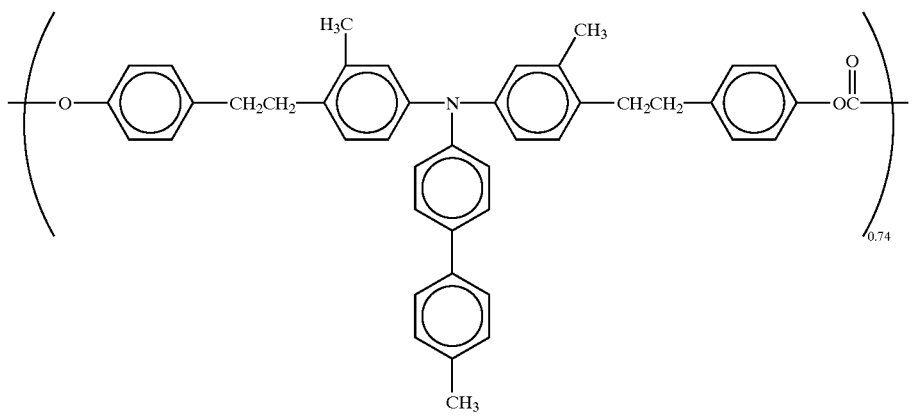
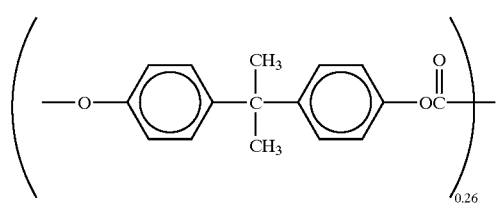

Polycarbonate of Example 17
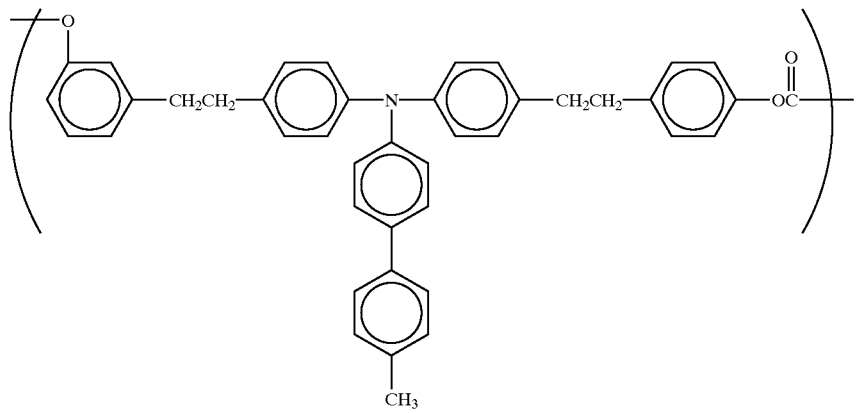
Polycarbonate of Example 18
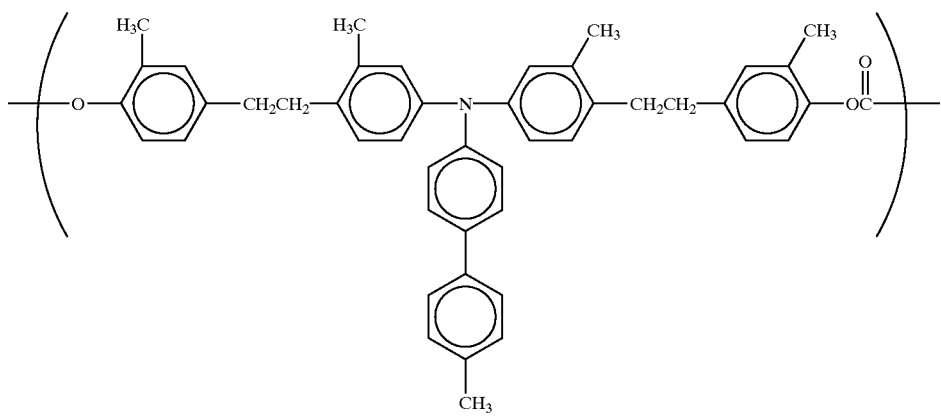
Polycarbonate of Example 19
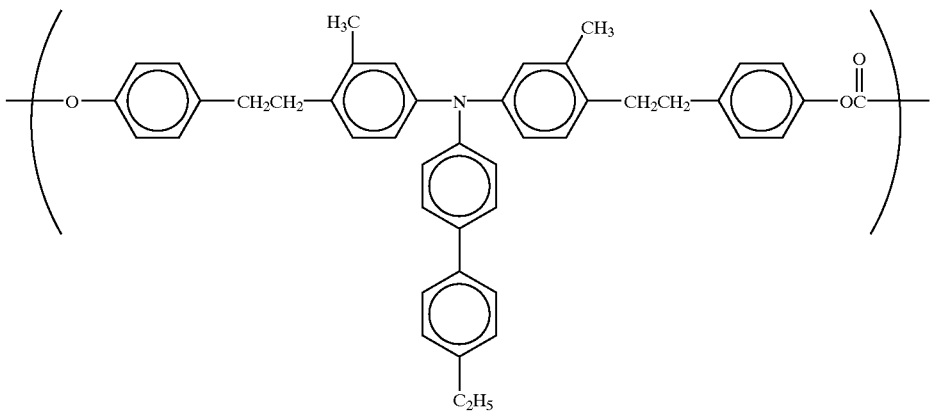

Polycarbonate of Example 20
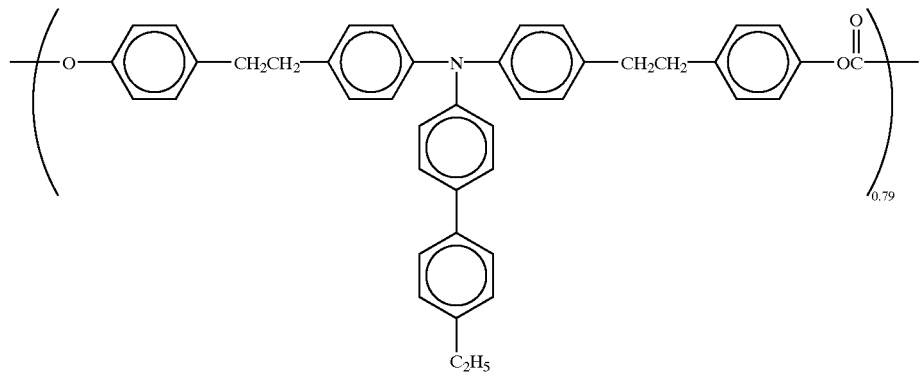
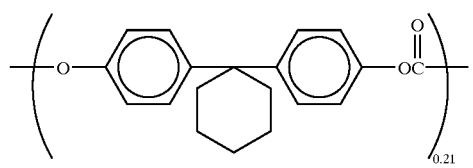
Polycarbonate of Example 21
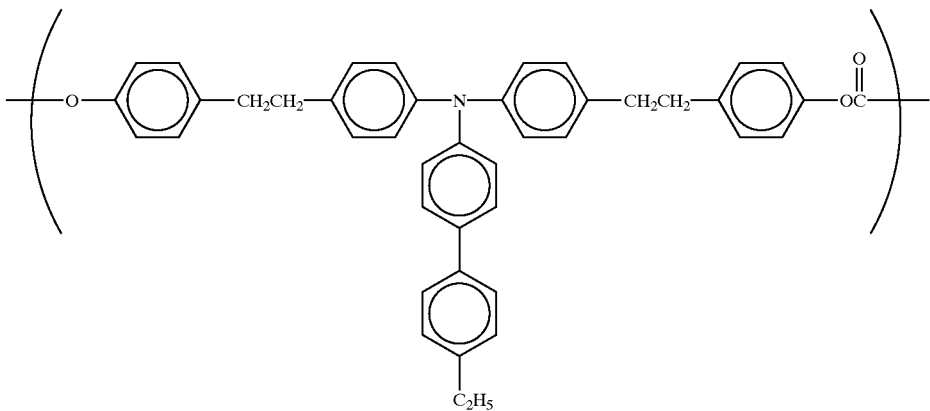
Polycarbonate of Example 22
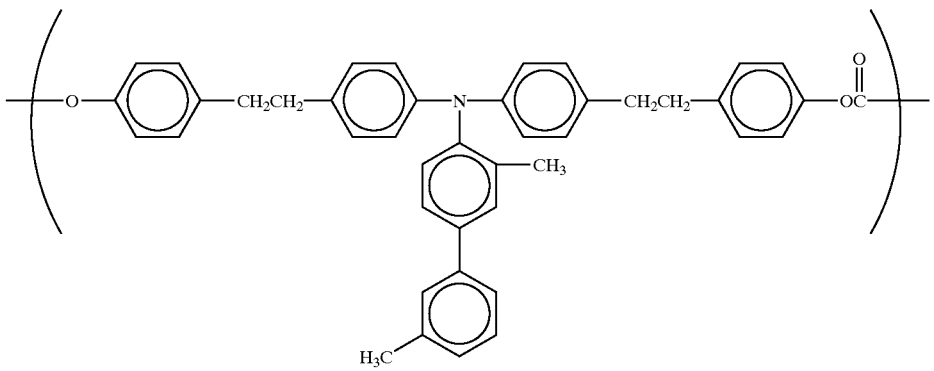

Polycarbonate of Example 23

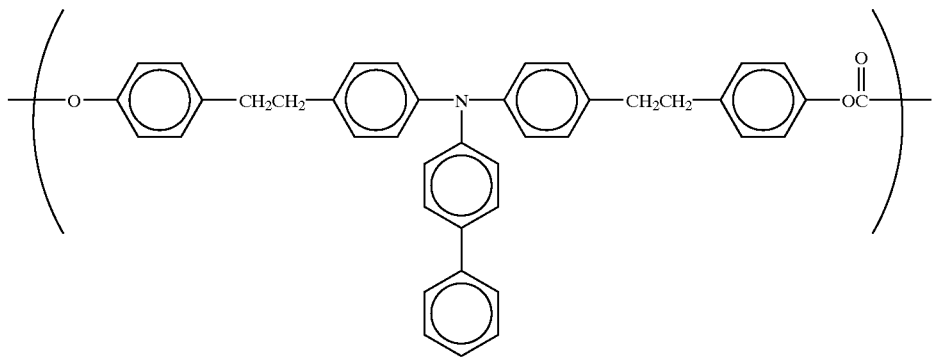

| Poly-Carbonate resin | Tg (°C.) | Elemental Anal. (%) obsd./calcd. | | | GPC | | |
|---|---|---|---|---|---|---|---|
| | | C | H | N | Mn × 10⁻⁴ | Mw × 10⁻⁴ | Mw/Mn |
| Example 15 | 141.2 | 83.19/ 82.98 | 6.24/ 6.27 | 2.21/ 1.94 | 5.13 | 15.0 | 2.94 |
| Example 16 | 145.2 | 82.71/ 82.86 | 6.16/ 6.15 | 2.12/ 1.94 | 5.62 | 14.7 | 2.60 |
| Example 17 | 124.5 | 83.98/ 83.86 | 6.03/ 6.07 | 2.44/ 2.28 | 3.52 | 16.5 | 4.68 |
| Example 18 | 132.8 | 84.06/ 83.97 | 6.59/ 6.60 | 2.24/ 2.13 | 3.88 | 21.9 | 5.63 |
| Example 19 | 139.2 | 84.19/ 83.94 | 6.45/ 6.43 | 2.15/ 2.18 | 4.90 | 19.3 | 3.94 |
| Example 20 | 146.7 | 83.29/ 83.15 | 6.02/ 6.07 | 1.74/ 2.02 | 5.04 | 16.8 | 3.34 |
| Example 21 | 143.8 | 84.10/ 83.87 | 6.02/ 6.06 | 2.09/ 2.27 | 5.58 | 19.3 | 3.47 |
| Example 22 | 130.8 | 83.81/ 83.88 | 6.03/ 6.06 | 2.39/ 2.28 | 3.48 | 10.0 | 2.90 |
| Example 23 | 142.7 | 83.83/ 83.78 | 5.7/ 5.67 | 2.41/ 2.38 | 3.38 | 11.7 | 3.45 |

EXAMPLE 24

A solution of polyamide resin (CM-8000, manufactured by Toray Industries, Inc.) dissolved in a mixed solvent of methanol and butanol was applied on an aluminum plate with a doctor blade and dried at room temperature to form an intermediate layer having a thickness of 0.3 μm. A dispersion liquid for a charge generation layer prepared by pulverizing and dispersing a bisazo compound as a charge generation material represented by the formula shown below in a mixed solvent of cyclohexanone and methyl ethyl ketone using a ball mill was coated on the intermediate layer with a doctor blade and dried at room temperature, whereby a charge generation layer having a thickness of about 0.5 μm was formed on the intermediate layer.

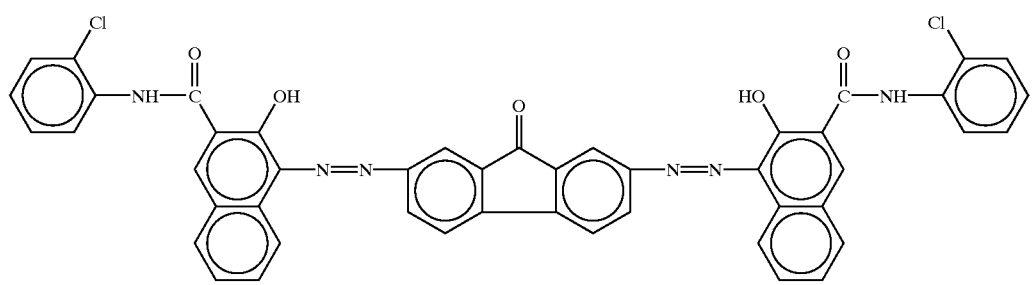

A solution obtained by dissolving the polycarbonate resin obtained in Example 9, serving as a charge transport material, in dichloromethane was coated on the charge generation layer with a doctor blade and dried at room temperature and then at 120° C. for 20 minutes to form a charge transport layer having a thickness of 20 μm on the charge generation layer.

The thus prepared photoconductor was charged in the dark under application of −6 kV of corona charge for 20 seconds using a commercially available electrostatic copying sheet testing apparatus ("Paper Analyzer Model SP-428" made by Kawaguchi Electro Works Co., Ltd.). The surface potential Vm (V) of the photoconductor was measured. Then, the photoconductor was allowed to stand in the dark for 20 seconds without applying any charge thereto, and the surface potential Vo (V) of the photoconductor was measured. The photoconductor was then illuminated by a tungsten lamp such that the illuminance on the illuminated surface of the photoconductor was 4.5 lux. The time (seconds) needed for the potential to become from −800 V to a half was measured and the exposure E1/2 (lux·sec) was calculated. The results are summarized in Table 2.

EXAMPLE 25–38

Photoconductors were prepared in the same manner as in Example 24 except that polycarbonate resins obtained in Example 10–23 were used in place of the polycarbonate resin of Example 9 and the evaluations were conducted in the same manner as in Example 24. The results are summarized in Table 2.

Using a commercially available electrophotographic copying machine, each of the above photoconductors was charged and exposed to light via an original image to form a latent electrostatic image thereon. Then, the latent electrostatic image was developed using a dry developer, and the thus obtained visible image (toner image) was transferred to a sheet of plain paper and fixed thereon. As a result, a clear toner transferred image was able to be obtained. When a wet developer was employed for the formation, a clear image was also able to be obtained.

TABLE 2

| Example | Polycarbonate resin | −Vm (V) | −Vo (V) | E1/2 (lux · sec) |
|---|---|---|---|---|
| 24 | Example 9 | 1464 | 1316 | 0.85 |
| 25 | Example 10 | 1292 | 1172 | 0.73 |
| 26 | Example 11 | 1509 | 1372 | 0.75 |
| 27 | Example 12 | 1613 | 1510 | 1.33 |
| 28 | Example 13 | 1364 | 1257 | 0.74 |
| 29 | Example 14 | 1533 | 1417 | 1.09 |
| 30 | Example 15 | 1587 | 1455 | 0.82 |
| 31 | Example 16 | 1543 | 1424 | 0.89 |
| 32 | Example 17 | 1524 | 1382 | 0.8 |
| 33 | Example 18 | 1618 | 1482 | 0.67 |
| 34 | Example 19 | 1478 | 1347 | 0.78 |
| 35 | Example 20 | 1619 | 1487 | 0.92 |
| 36 | Example 21 | 1589 | 1460 | 0.83 |
| 37 | Example 22 | 1637 | 1451 | 0.75 |
| 38 | Example 23 | 1562 | 1342 | 0.75 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

The teachings of Japanese Patent Application No. 2000-368297, filed Dec. 4, 2000, inclusive of the specification, claims and drawings, are hereby incorporated by reference herein.

What is claimed is:

1. A diphenol compound comprising:
   at least one triarylamine group,
   two divalent alkane groups each having two, first and second bonds, said first bond of each of said alkane groups being bonded to separate one of the aryl groups of said at least one triarylamine group,
   an aryl group bonded to the second bond of each of said two alkane groups, and
   a hydroxyl group bonded to each of the aryl groups linked to said two alkane groups.

2. A diphenol compound represented by the following formula (1):

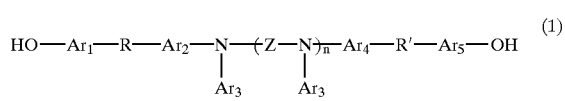

wherein $Ar_1$, $Ar_2$, $Ar_4$ and $Ar_5$ stand, independently from each other, for an arylene group or a substituted arylene group, $Ar_3$ stands for an aryl group or a substituted aryl group, Z stands for an arylene group or —$Ar_6$—Za—$Ar_6$— where $Ar_6$ represents an arylene group or a substituted arylene group and Za represents —O—, —S— or an alkylene group, R and R' stand, independently from each other, for a straight chain alkylene group or a branched alkylene group and n is an integer of 0 or 1.

3. A diphenol compound according to claim 2 and represented by the following formula (2):

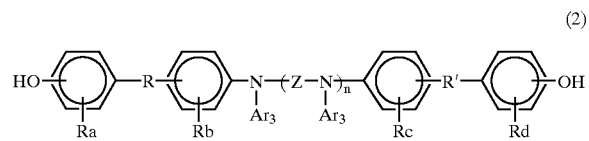

wherein Ra, Rb, Rc and Rd stand for an alkyl group and $Ar_3$, Z, R, R' and n are as defined above.

4. An aromatic polycarbonate resin comprising a main structural unit represented by the following formula (3):

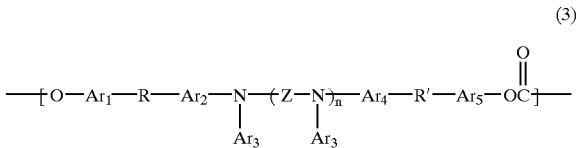

wherein $Ar_1$, $Ar_2$, $Ar_4$ and $Ar_5$ stand, independently from each other, for an arylene group or a substituted arylene group, $Ar_3$ stands for an aryl group or a substituted aryl group, Z stands for an arylene group or —$Ar_6$—Za—$Ar_6$— where $Ar_6$ represents an arylene group or a substituted arylene group and Za represents —O—, —S— or an alkylene group, R and R' stand, independently from each other, for a straight chain alkylene group or a branched alkylene group and n is an integer of 0 or 1.

5. An aromatic polycarbonate resin according to claim 4, wherein said main structural unit is represented by the following formula (4):

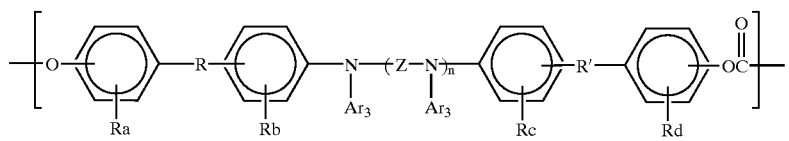

(4)

wherein Ra, Rb, Rc and Rd stand for an alkyl group and Ar$_3$, Z, R, R' and n are as defined above.

6. An aromatic polycarbonate resin according to claim 4, further comprising an additional structural unit represented by the formula (5):

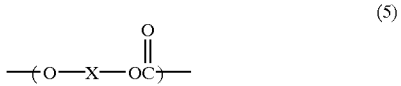

(5)

wherein X is a group selected from the group consisting of divalent aliphatic groups, substituted divalent aliphatic groups, divalent alicyclic groups, substituted divalent alicyclic groups, divalent aromatic groups, substituted divalent aromatic groups, divalent groups obtained by linking at least two of the foregoing groups and groups represented by the following formulas:

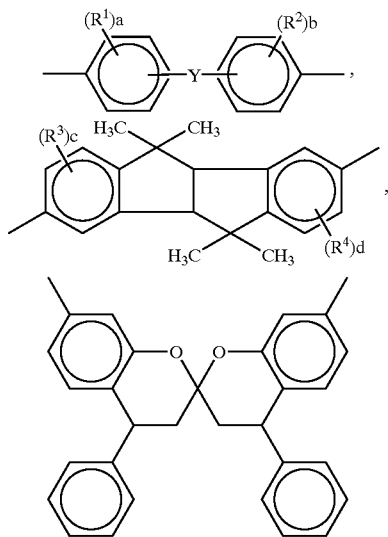

wherein R$^1$, R$^2$, R$^3$ and R$^4$ stand, independently from each other, for an alkyl group, a substituted alkyl group, an aryl group, a substituted aryl group or a halogen atom, a and b are independently an integer of 0–4, c and d are independently an ingeger of 0–3, Y is selected from the group consisting of a direct bond, straight chain alkylene groups having 2–12 carbon atoms, substituted straight chain alkylene groups having 2–12 carbon atoms, branched chain alkylene groups having 3–12 carbon atoms, substituted branched chain alkylene groups having 3–12 carbon atoms, divalent groups composed of at least one alkylene group having 1–10 carbon atoms and at least one —O— or at least one —S—, —O—, —S—, —SO—, —SO$_2$—, —CO—, —COO— and groups represented by the following formulas:

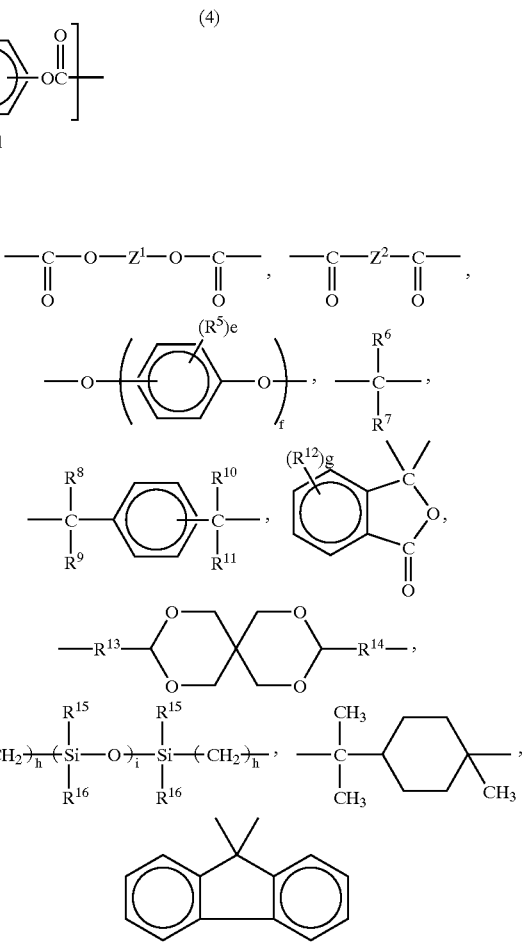

in which Z$^1$ and Z$^2$ stand independently from each other for a divalent aliphatic group, a substituted divalent aliphatic group, an arylene group or a substituted arylene group; R$^5$, R$^6$ and R$^{12}$ stand independently from each other for a halogen atom, an alkyl group, a substituted alkyl group, an alkoxyl group, a substituted alkoxyl group, an aryl group or a substituted aryl group, R$^7$, R$^8$, R$^9$, R$^{10}$ and R$^{11}$ stand independently from each other for a hdyrogen atom, R$^6$ and R$^7$ may form a carbocyclic ring having 5 to 12 carbon atoms together, R$^{13}$ and R$^{14}$ stand independently from each other for a direct bond or an alkylene group having 1–4 carbon atoms, R$^{15}$ and R$^{16}$ stand independently from each other an alkyl group, a substituted alkyl group, an aryl group or a substituted aryl group, e and g are each an integer of 0–4, f is an integer of 1 or 2, h is an integer of 0–20 and i is an integer of 0–2000, wherein said main structural unit and said additional structural are present in such a proportion that satisfies the following condition:

$0 < k/(k+j) \leq 1$ wherein k and j are molar fractions of said main structural unit and said additional structural unit in said aromatic polycarbonate resin, respectively.

7. A polycarbonate resin according to claim 6, wherein said main structural unit represented by the formula (3) is represented by the following formula (4):

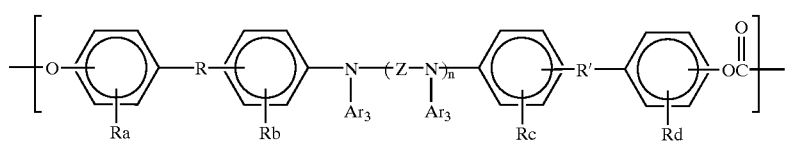

wherein Ra, Rb, Rc and Rd stand for an alkyl group and Ar$_3$, Z, R, R' and n are as defined above.

8. A polycarbonate resin comprising a recurring unit represented by the following formula (6):

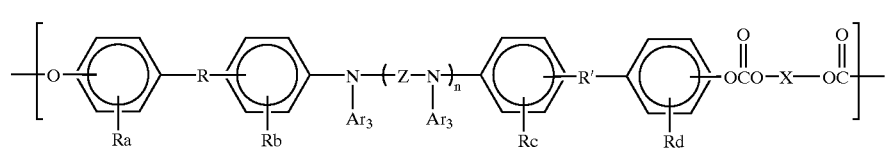

wherein Ra, Rb, Rc and Rd stand for an alkyl group, Ar$_3$ stands for an aryl group or a substituted aryl group, Z stands for an arylene group or —Ar$_6$—Za—Ar$_6$— where Ar$_6$ represents an arylene group or a substituted arylene group and Za represents —O—, —S— or an alkylene group, R and R' stand, independently from each other, for a straight chain alkylene group or a branched alkylene group, n is an integer of 0 or 1 and X stands for a group selected from the group consisting of divalent aliphatic groups, substituted divalent aliphatic groups, divalent alicyclic groups, substituted divalent alicyclic groups, divalent aromatic groups, substituted divalent aromatic groups, divalent groups obtained by linking at least two of the foregoing groups and groups represented by the following formulas:

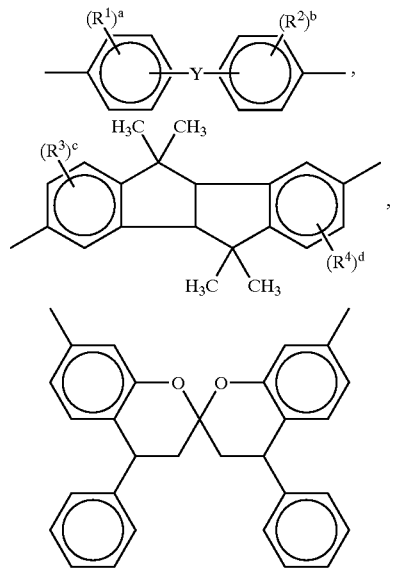

wherein R$^1$, R$^2$, R$^3$ and R$^4$ stand, independently from each other, for an alkyl group, a substituted alkyl group, an aryl group, a substituted aryl group or a halogen atom, a and b are independently an integer of 0–4, c and d are independently an integer of 0–3, Y is selected from the group consisting of a direct bond, straight chain alkylene groups having 2–12 carbon atoms, substituted straight chain alkylene groups having 2–12 carbon atoms, branched chain alkylene groups having 3–12 carbon atoms, substituted branched chain alkylene groups having 3–12 carbon atoms, divalent groups composed of at least one alkylene group having 1–10 carbon atoms and at least one —O— or at least one —S—, —O—, —S—, —SO—, —SO$_2$—, —CO—, —COO— and groups represented by the following formulas:

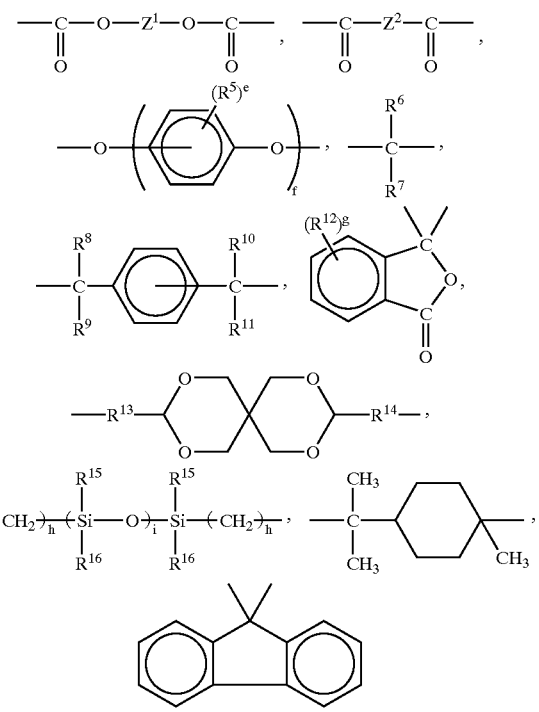

wherein Z$^1$ and Z$^2$ stand independently from each other for a divalent aliphatic group, a substituted divalent aliphatic group, an arylene group or a substituted arylene group; R$^5$, R$^6$ and R$^{12}$ stand independently from each other for a halogen atom, an alkyl group, a substituted alkyl group, an alkoxyl group, a substituted alkoxyl group, an aryl group or a substituted aryl group, R$^7$, R$^8$, R$^9$, R$^{10}$ and R$^{11}$ stand independently from each other for a hydrogen atom, R$^6$ and R$^7$ may form a carbocyclic ring having 5 to 12 carbon atoms together, R$^{13}$ and R$^{14}$ stand independently from each other for a direct bond or an alkylene group having 1–4 carbon atoms, R$^{15}$ and R$^{16}$ stand independently from each other an alkyl group, a substituted alkyl group, an aryl group or a substituted aryl group, e and g are each an integer of 0–4, f is an integer of 1 or 2, h is an integer of 0–20 and i is an integer of 0–2000.

9. An electrophotographic photoconductor comprising an electroconductive support, and a photoconductive layer provided on said support and comprising an aromatic polycarbonate resin having a recurring unit comprising:

at least one triarylamine group, a divalent alkane group having two, first and second bonds, said first bond being bonded to one of the aryl groups of said at least one triarylamine group, a non-triarylamine aryl group bonded to said second bond of said alkane group, and a carbonyldioxy group bonded to said aryl group that is bonded to said second bond of said alkane group.

10. An electrophotographic photoconductor comprising an electroconductive support, and a photoconductive layer provided on said support and comprising an aromatic polycarbonate resin having a main structural unit represented by the following formula (3):

(3)

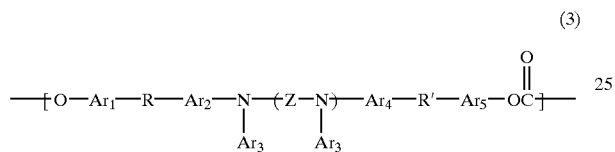

wherein $Ar_1$, $Ar_2$, $Ar_4$ and $Ar_5$ stand, independently from each other, for an arylene group or a substituted arylene group, $Ar_3$ stands for an aryl group or a substituted aryl group, Z stands for an arylene group or —$Ar_6$—Za—$Ar_6$— where $Ar_6$ represents an arylene group or a substituted arylene group and Za represents—O—, —S— or an alkylene group, R and R' stand, independently from each other, for a straight chain alkylene group or a branched alkylene group and n is an integer of 0 or 1.

11. An electrophotographic photoconductor as claimed in claim 10, wherein said main structural unit is represented by the following formula (4):

(4)

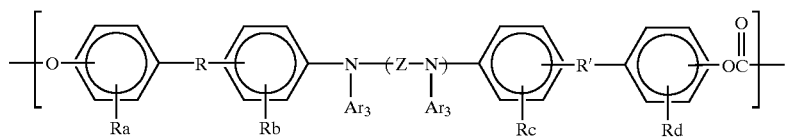

wherein Ra, Rb, Rc and Rd stand for an alkyl group and $Ar_3$, Z, R, R' and n are as defined above.

12. An electrophotographic photoconductor as claimed in claim 10, wherein said aromatic polycarbonate resin further comprises an additional structural unit represented by the formula (5):

(5)

wherein X is a group selected from the group consisting of divalent aliphatic groups, substituted divalent aliphatic groups, divalent alicyclic groups, substituted divalent alicyclic groups, divalent aromatic groups, substituted divalent aromatic groups, divalent groups obtained by linking at least two of the foregoing groups and groups represented by the following formulas:

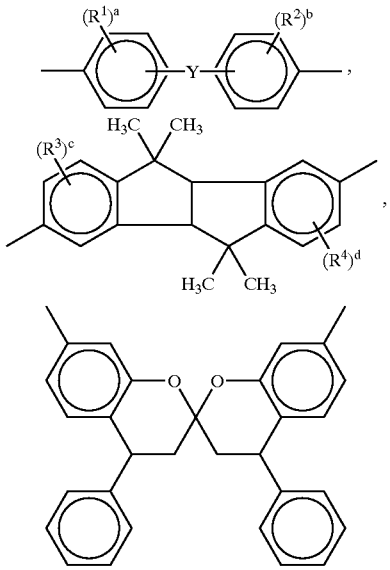

wherein $R^1$, $R^2$, $R^3$ and $R^4$ stand, independently from each other, for an alkyl group, a substituted alkyl group, an aryl group, a substituted aryl group or a halogen atom, a and b are independently an integer of 0–4, c and d are independently an ingeger of 0–3, Y is selected from the group consisting of a direct bond, straight chain alkylene groups having 2–12 carbon atoms, substituted straight chain alkylene groups having 2–12 carbon atoms, branched chain alkylene groups having 3–12 carbon atoms, substituted branched chain alkylene groups having 3–12 carbon atoms, divalent groups composed of at least one alkylene group having 1–10 carbon atoms and at least one —O— or at least one —S—, —O—, —S—, —SO—, —SO$_2$—, —CO—, —COO— and groups represented by the following formulas:

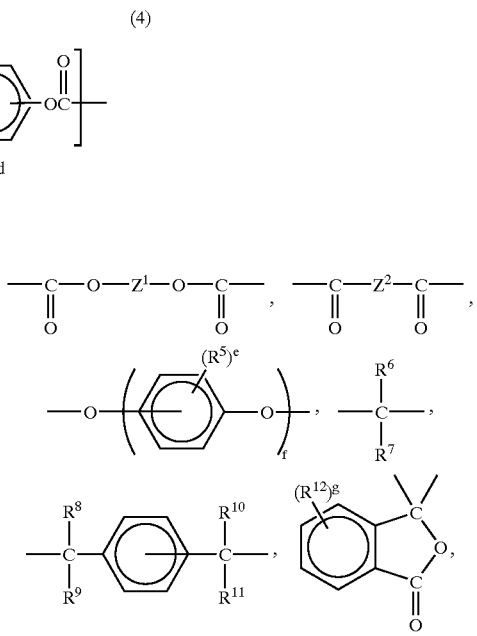

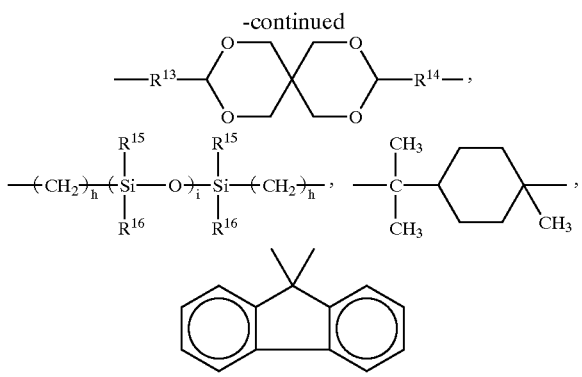

wherein $Z^1$ and $Z^2$ stand independently from each other for a divalent aliphatic group, a substituted divalent aliphatic group, an arylene group or a substituted arylene group; $R^5$, $R^6$ and $R^{12}$ stand independently from each other for a halogen atom, an alkyl group, a substituted alkyl group, an alkoxyl group, a substituted alkoxyl group, an aryl group or a substituted aryl group, $R^7$, $R^8$, $R^9$, $R^{10}$ and $R^{11}$ stand independently from each other for a hdyrogen atom, $R^6$ and $R^7$ may form a carbocyclic ring having 5 to 12 carbon atoms together, $R^{13}$ and $R^{14}$ stand independently from each other for a direct bond or an alkylene group having 1–4 carbon atoms, $R^{15}$ and $R^{16}$ stand independently from each other an alkyl group, a substituted alkyl group, an aryl group or a substituted aryl group, e and g are each an integer of 0–4, f is an integer of 1 or 2, h is an integer of 0–20 and i is an integer of 0–2000, wherein said main structural unit and said additional structural are present in such a proportion that satisfies the following condition:

$$0 < k/(k+j) \leq 1$$

wherein k and j are molar fractions of said main structural unit and said additional structural unit in said aromatic polycarbonate resin, respectively.

13. An electrophotographic photoconductor according to claim 12, wherein said main structural unit represented by the formula (3) is represented by the following formula (4):

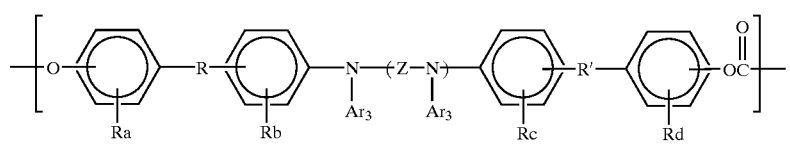

(4)

wherein Ra, Rb, Rc and Rd stand for an alkyl group and $Ar_3$, Z, R, R' and n are as defined above.

14. An electrophotographic photoconductor comprising an electroconductive support, and a photoconductive layer provided on said support and comprising a polycarbonate resin having a recurring unit represented by the following formula (6):

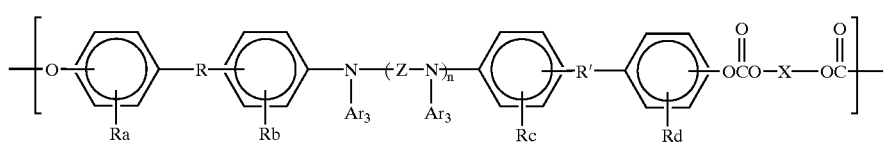

(6)

wherein Ra, Rb, Rc and Rd stand for an alkyl group, $Ar_3$ stands for an aryl group or a substituted aryl group, Z stands for an arylene group or —$Ar_6$—Za—$Ar_6$— where $Ar_6$ represents an arylene group or a substituted arylene group and Za represents —O—, —S— or an alkylene group, R and R' stand, independently from each other, for a straight chain alkylene group or a branched alkylene group, n is an integer of 0 or 1 and X stands for a group selected from the group consisting of divalent aliphatic groups, substituted divalent aliphatic groups, divalent alicyclic groups, substituted divalent alicyclic groups, divalent aromatic groups, substituted divalent aromatic groups, divalent groups obtained by linking at least two of the foregoing groups and groups represented by the following formulas:

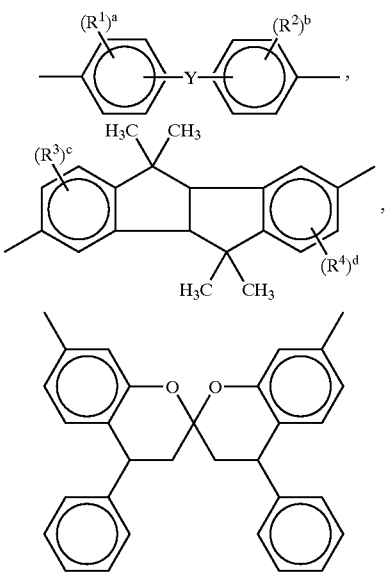

wherein $R^1$, $R^2$, $R^3$ and $R^4$ stand, independently from each other, for an alkyl group, a substituted alkyl group, an aryl group, a substituted aryl group or a halogen atom, a and b are independently an integer of 0–4, c and d are independently an ingeger of 0–3, Y is selected from the group consisting of a direct bond, straight chain alkylene groups having 2–12 carbon atoms, substituted straight chain alkylene groups having 2–12 carbon atoms, branched chain alkylene groups having 3–12 carbon atoms, substituted branched chain alkylene groups having 3–12 carbon atoms, divalent groups composed of at least one alkylene group having 1–10 carbon atoms and at least one —O— or at least one —S—, —O—, —S—, —SO—, —SO$_2$—, —CO—, —COO— and groups represented by the following formulas:

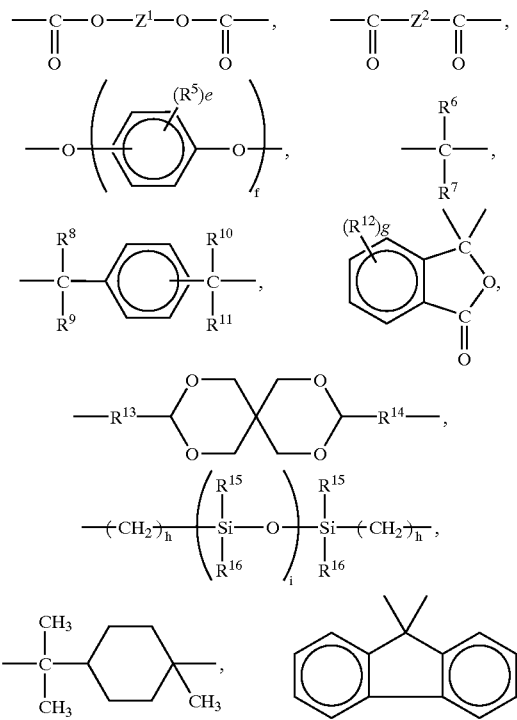

wherein $Z^1$ and $Z^2$ stand independently from each other for a divalent aliphatic group, a substituted divalent aliphatic group, an arylene group or a substituted arylene group; $R^5$, $R^6$ and $R^{12}$ stand independently from each other for a halogen atom, an alkyl group, a substituted alkyl group, an alkoxyl group, a substituted alkoxyl group, an aryl group or a substituted aryl group, $R^7$, $R^8$, $R^9$, $R^{10}$ and $R^{11}$ stand independently from each other for a hdyrogen atom, $R^6$ and $R^7$ may form a carbocyclic ring having 5 to 12 carbon atoms together, $R^{13}$ and $R^{14}$ stand independently from each other for a direct bond or an alkylene group having 1–4 carbon atoms, $R^{15}$ and $R^{16}$ stand independently from each other an alkyl group, a substituted alkyl group, an aryl group or a substituted aryl group, e and g are each an integer of 0–4, f is an integer of 1 or 2, h is an integer of 0–20 and i is an integer of 0–2000.

15. An electrophotographic process comprising charging an electrophotographic photoconductor according to claim 10, exposing the photoconductor to light to form an electrostatic image thereon, developing the electrostatic image, and transferring the developed image to a transfer medium.

16. An electrophotographic process as claimed in claim 15, wherein said exposing is performed based on digital information using light emitting diode or semiconductor laser.

17. An electrophotographic apparatus comprising an electrophotographic photoconductor according to claim 10, means for charging the photoconductor, means for exposing the photoconductor to form an electrostatic image thereon, means for developing the electrostatic image on the photoconductor, and means for transferring the developed image to a transfer medium.

18. An electrophotographic apparatus as claimed in claim 17, wherein said exposing means comprises light emitting diode or semiconductor laser to perform the exposure based on digital information.

19. An electrophotographic process cartridge comprising an electrophotographic photoconductor according to claim 10.

* * * * *